(12) United States Patent
Stark et al.

(10) Patent No.: US 8,941,083 B2
(45) Date of Patent: *Jan. 27, 2015

(54) APPLYING A PARTICLE BEAM TO A PATIENT

(75) Inventors: James M. Stark, Worcester, MA (US); Stanley J. Rosenthal, Wayland, MA (US); Miles S. Wagner, Brookline, MA (US); Michael J. Ahearn, Sandown, NH (US)

(73) Assignee: Mevion Medical Systems, Inc., Littleton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/213,014

(22) Filed: Aug. 18, 2011

(65) Prior Publication Data

US 2011/0299919 A1    Dec. 8, 2011

Related U.S. Application Data

(63) Continuation of application No. 11/870,961, filed on Oct. 11, 2007, now Pat. No. 8,003,964.

(51) Int. Cl.
*A61N 5/10* (2006.01)
*G21K 5/04* (2006.01)

(52) U.S. Cl.
CPC ............... *A61N 5/1042* (2013.01); *G21K 5/04* (2013.01)
USPC .................................... 250/492.3; 250/505.1

(58) Field of Classification Search
USPC ........................................... 250/492.3, 505.1
See application file for complete search history.

(56) References Cited

U.S. PATENT DOCUMENTS

| | | | |
|---|---|---|---|
| 2,280,606 A | 4/1942 | Van et al. | |
| 2,492,324 A | 12/1949 | Salisbury | |
| 2,615,129 A | 10/1952 | McMillan | |
| 2,659,000 A | 11/1953 | Salisbury | |
| 3,175,131 A | 3/1965 | Burleigh et al. | |
| 3,432,721 A | 3/1969 | Naydan et al. | |
| 3,582,650 A | 6/1971 | Avery | |
| 3,679,899 A | 7/1972 | Dimeff | |

(Continued)

FOREIGN PATENT DOCUMENTS

| | | |
|---|---|---|
| CA | 2629333 | 5/2007 |
| DE | 2753397 | 6/1978 |

(Continued)

OTHER PUBLICATIONS

Tilly, Nina, et al., "Development and verification of the pulsed scanned proton beam at The Svedberg Laboratory in Uppsala", Phys. Med. Biol. 52, 2741-2754, 2007 (14 pages).

(Continued)

*Primary Examiner* — Jack Berman
(74) *Attorney, Agent, or Firm* — Fish & Richardson P.C.

(57) ABSTRACT

An apparatus includes a yoke having a first end and a second end. The yoke is configured to hold a device that includes an aperture and a range compensation structure. A catch arm is pivotally secured to the first end of the yoke. The catch arm includes a locking feature. The locking feature and the second end of the yoke interface, respectively, to a first retention feature and a second retention feature defined by the aperture and the range compensation structure. The locking feature is configured to interface to the first retention feature and the second end of the yoke is configured to interface to the second retention feature.

17 Claims, 16 Drawing Sheets

(56) References Cited

U.S. PATENT DOCUMENTS

| | | |
|---|---|---|
| 3,689,847 A | 9/1972 | Verster |
| 3,720,817 A * | 3/1973 | Dinwiddie ............... 600/1 |
| 3,757,118 A | 9/1973 | Hodge et al. |
| 3,868,522 A | 2/1975 | Bigham et al. |
| 3,886,367 A | 5/1975 | Castle |
| 3,925,676 A | 12/1975 | Bigham et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Taumann et al. |
| 4,230,129 A | 10/1980 | LeVeen |
| 4,256,966 A | 3/1981 | Heinz |
| 4,336,505 A | 6/1982 | Meyer |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,629,893 A * | 12/1986 | Hanz et al. ............ 250/505.1 |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,902,993 A | 2/1990 | Krevet |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,987,309 A | 1/1991 | Klasen et al. |
| 4,996,496 A | 2/1991 | Kitamura et al. |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,148,032 A | 9/1992 | Hernandez |
| 5,166,531 A | 11/1992 | Huntzinger |
| 5,189,687 A | 2/1993 | Bova et al. |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,405,235 A | 4/1995 | Lebre et al. |
| 5,440,133 A | 8/1995 | Moyers et al. |
| 5,461,773 A | 10/1995 | Kawaguchi |
| 5,463,291 A | 10/1995 | Carroll et al. |
| 5,511,549 A | 4/1996 | Legg et al. |
| 5,521,469 A | 5/1996 | Laisne |
| 5,561,697 A | 10/1996 | Takafuji et al. |
| 5,585,642 A | 12/1996 | Britton et al. |
| 5,633,747 A | 5/1997 | Nikoonahad |
| 5,668,371 A | 9/1997 | Deasy et al. |
| 5,726,448 A | 3/1998 | Smith et al. |
| 5,751,781 A | 5/1998 | Brown et al. |
| 5,778,047 A | 7/1998 | Mansfield et al. |
| 5,811,944 A | 9/1998 | Sampayan et al. |
| 5,818,058 A | 10/1998 | Nakanishi et al. |
| 5,821,705 A | 10/1998 | Caporaso et al. |
| 5,825,845 A | 10/1998 | Blair et al. |
| 5,841,237 A | 11/1998 | Alton |
| 5,846,043 A | 12/1998 | Spath |
| 5,851,182 A | 12/1998 | Sahadevan |
| 5,866,912 A | 2/1999 | Slater et al. |
| 5,874,811 A | 2/1999 | Finlan et al. |
| 5,895,926 A | 4/1999 | Britton et al. |
| 5,920,601 A | 7/1999 | Nigg et al. |
| 5,929,458 A | 7/1999 | Nemezawa et al. |
| 5,993,373 A | 11/1999 | Nonaka et al. |
| 6,034,377 A | 3/2000 | Pu |
| 6,057,655 A | 5/2000 | Jongen |
| 6,061,426 A | 5/2000 | Linders et al. |
| 6,064,807 A | 5/2000 | Arai et al. |
| 6,080,992 A * | 6/2000 | Nonaka et al. ............ 250/505.1 |
| 6,094,760 A | 8/2000 | Nonaka et al. |
| 6,140,021 A | 10/2000 | Nakasuji et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riaziat et al. |
| 6,316,776 B1 | 11/2001 | Hiramoto et al. |
| 6,380,545 B1 | 4/2002 | Yan |
| 6,407,505 B1 | 6/2002 | Bertsche |
| 6,433,336 B1 | 8/2002 | Jongen et al. |
| 6,433,349 B2 | 8/2002 | Akiyama et al. |
| 6,441,569 B1 | 8/2002 | Janzow |
| 6,443,349 B1 | 9/2002 | Van Der Burg |
| 6,476,403 B1 | 11/2002 | Dolinskii et al. |
| 6,492,922 B1 | 12/2002 | New |
| 6,501,981 B1 | 12/2002 | Schweikard et al. |
| 6,519,316 B1 | 2/2003 | Collins |
| 6,621,889 B1 | 9/2003 | Mostafavi |
| 6,646,383 B2 | 11/2003 | Bertsche et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,717,162 B1 | 4/2004 | Jongen |
| 6,769,806 B2 | 8/2004 | Moyers |
| 6,774,383 B2 | 8/2004 | Norimine et al. |
| 6,777,700 B2 | 8/2004 | Yanagisawa et al. |
| 6,800,866 B2 | 10/2004 | Amemiya et al. |
| 6,803,591 B2 | 10/2004 | Muramatsu et al. |
| 6,814,694 B1 | 11/2004 | Pedroni |
| 6,853,703 B2 | 2/2005 | Svatos et al. |
| 6,865,254 B2 | 3/2005 | Nafstadius |
| 6,891,177 B1 | 5/2005 | Kraft et al. |
| 6,897,451 B2 | 5/2005 | Kaercher et al. |
| 6,914,396 B1 | 7/2005 | Symons et al. |
| 6,953,943 B2 | 10/2005 | Yanagisawa et al. |

(56) References Cited

U.S. PATENT DOCUMENTS

| | | |
|---|---|---|
| 6,965,116 B1 | 11/2005 | Wagner et al. |
| 6,969,194 B1 | 11/2005 | Nafstadius |
| 6,984,835 B2 | 1/2006 | Harada |
| 6,993,112 B2 | 1/2006 | Hesse |
| 7,008,105 B2 | 3/2006 | Amann et al. |
| 7,014,361 B1 | 3/2006 | Ein-Gal |
| 7,026,636 B2 | 4/2006 | Yanagisawa et al. |
| 7,045,781 B2 | 5/2006 | Adamec et al. |
| 7,053,389 B2 | 5/2006 | Yanagisawa et al. |
| 7,071,479 B2 | 7/2006 | Yanagisawa et al. |
| 7,071,749 B2 | 7/2006 | Gardner |
| 7,091,478 B2 | 8/2006 | Haberer |
| 7,135,678 B2 | 11/2006 | Wang et al. |
| 7,138,771 B2 | 11/2006 | Bechthold et al. |
| 7,154,108 B2 | 12/2006 | Tadokoro et al. |
| 7,162,005 B2 | 1/2007 | Bjorkholm |
| 7,173,385 B2 | 2/2007 | Caporaso et al. |
| 7,208,748 B2 | 4/2007 | Sliski et al. |
| 7,247,869 B2 | 7/2007 | Tadokoro et al. |
| 7,274,018 B2 | 9/2007 | Adamec et al. |
| 7,295,649 B2 | 11/2007 | Johnsen |
| 7,297,967 B2 | 11/2007 | Yanagisawa et al. |
| 7,318,805 B2 | 1/2008 | Schweikard et al. |
| 7,319,336 B2 | 1/2008 | Baur et al. |
| 7,348,557 B2 | 3/2008 | Armit |
| 7,348,579 B2 | 3/2008 | Pedroni |
| 7,355,189 B2 | 4/2008 | Yanagisawa et al. |
| 7,402,963 B2 | 7/2008 | Sliski |
| 7,453,076 B2 | 11/2008 | Welch et al. |
| 7,466,085 B2 | 12/2008 | Nutt |
| 7,468,506 B2 | 12/2008 | Rogers et al. |
| 7,473,913 B2 | 1/2009 | Hermann et al. |
| 7,476,883 B2 | 1/2009 | Nutt |
| 7,525,104 B2 | 4/2009 | Harada |
| 7,541,905 B2 | 6/2009 | Antaya |
| 7,554,096 B2 | 6/2009 | Ward et al. |
| 7,554,097 B2 | 6/2009 | Ward et al. |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 7,579,603 B2 | 8/2009 | Birgy et al. |
| 7,582,885 B2 | 9/2009 | Katagiri et al. |
| 7,582,886 B2 | 9/2009 | Trbojevic |
| 7,598,497 B2 | 10/2009 | Yamamoto et al. |
| 7,629,598 B2 | 12/2009 | Harada |
| 7,656,258 B1 | 2/2010 | Antaya et al. |
| 7,659,528 B2 | 2/2010 | Uematsu |
| 7,692,166 B2 | 4/2010 | Muraki et al. |
| 7,696,847 B2 | 4/2010 | Antaya |
| 7,728,311 B2 | 6/2010 | Gall |
| 7,759,642 B2 | 7/2010 | Nir |
| 7,770,231 B2 | 8/2010 | Prater et al. |
| 7,786,451 B2 | 8/2010 | Ward et al. |
| 7,786,452 B2 | 8/2010 | Ward et al. |
| 7,807,982 B2 | 10/2010 | Nishiuchi et al. |
| 7,816,657 B2 | 10/2010 | Hansmann et al. |
| 7,834,334 B2 | 11/2010 | Grozinger et al. |
| 7,834,336 B2 | 11/2010 | Boeh et al. |
| 7,848,488 B2 | 12/2010 | Mansfield |
| 7,857,756 B2 | 12/2010 | Warren et al. |
| 7,894,574 B1 | 2/2011 | Nord et al. |
| 7,914,734 B2 | 3/2011 | Livingston |
| 7,919,765 B2 | 4/2011 | Timmer |
| 7,920,672 B2 | 4/2011 | Timmer |
| 7,928,415 B2 | 4/2011 | Bert et al. |
| 7,943,913 B2 | 5/2011 | Balakin |
| 7,950,587 B2 | 5/2011 | Henson et al. |
| 7,977,648 B2 | 7/2011 | Westerly et al. |
| 7,982,198 B2 | 7/2011 | Nishiuchi et al. |
| 7,986,768 B2 | 7/2011 | Nord et al. |
| 7,990,524 B2 | 8/2011 | Jureller et al. |
| 8,003,964 B2 * | 8/2011 | Stark et al. ................. 250/505.1 |
| 8,009,804 B2 | 8/2011 | Nord et al. |
| 8,041,006 B2 | 10/2011 | Boyden et al. |
| 8,053,508 B2 | 11/2011 | Korkut et al. |
| 8,053,745 B2 | 11/2011 | Moore |
| 8,053,746 B2 | 11/2011 | Timmer et al. |
| 8,067,748 B2 | 11/2011 | Balakin |
| 8,085,899 B2 | 12/2011 | Nord et al. |
| 8,089,054 B2 | 1/2012 | Balakin |
| 8,093,564 B2 | 1/2012 | Balakin |
| 8,093,568 B2 | 1/2012 | Mackie et al. |
| 8,129,699 B2 | 3/2012 | Balakin |
| 8,144,832 B2 | 3/2012 | Balakin |
| 8,153,989 B2 | 4/2012 | Tachikawa et al. |
| 8,173,981 B2 | 5/2012 | Trbojevic |
| 8,188,688 B2 | 5/2012 | Balakin |
| 8,198,607 B2 | 6/2012 | Balakin |
| 8,227,768 B2 | 7/2012 | Smick et al. |
| 8,232,536 B2 | 7/2012 | Harada |
| 8,288,742 B2 | 10/2012 | Balakin |
| 8,294,127 B2 | 10/2012 | Tachibana |
| 8,304,725 B2 | 11/2012 | Komuro et al. |
| 8,304,750 B2 | 11/2012 | Preikszas et al. |
| 8,309,941 B2 | 11/2012 | Balakin |
| 8,330,132 B2 | 12/2012 | Guertin et al. |
| 8,334,520 B2 | 12/2012 | Otaka et al. |
| 8,335,397 B2 | 12/2012 | Takane et al. |
| 8,344,340 B2 | 1/2013 | Gall et al. |
| 8,350,214 B2 | 1/2013 | Otaki et al. |
| 8,368,038 B2 | 2/2013 | Balakin |
| 8,373,143 B2 | 2/2013 | Balakin |
| 8,373,145 B2 | 2/2013 | Balakin |
| 8,378,299 B2 | 2/2013 | Frosien |
| 8,378,321 B2 | 2/2013 | Balakin |
| 8,382,943 B2 | 2/2013 | Clark |
| 8,399,866 B2 | 3/2013 | Balakin |
| 8,405,042 B2 | 3/2013 | Honda et al. |
| 8,405,056 B2 | 3/2013 | Amaldi et al. |
| 8,415,643 B2 | 4/2013 | Balakin |
| 8,416,918 B2 | 4/2013 | Nord et al. |
| 8,421,041 B2 | 4/2013 | Balakin |
| 8,426,833 B2 | 4/2013 | Trbojevic |
| 8,436,323 B2 | 5/2013 | Iseki et al. |
| 8,440,987 B2 | 5/2013 | Stephani et al. |
| 8,445,872 B2 | 5/2013 | Behrens et al. |
| 8,466,441 B2 | 6/2013 | Iwata et al. |
| 8,472,583 B2 | 6/2013 | Star-Lack et al. |
| 8,483,357 B2 | 7/2013 | Siljamaki et al. |
| 8,487,278 B2 | 7/2013 | Balakin |
| 8,552,406 B2 | 10/2013 | Phaneuf et al. |
| 8,552,408 B2 | 10/2013 | Hanawa et al. |
| 8,569,717 B2 | 10/2013 | Balakin |
| 8,581,215 B2 | 11/2013 | Balakin |
| 8,653,314 B2 | 2/2014 | Pelati et al. |
| 8,653,473 B2 | 2/2014 | Yajima |
| 2003/0048080 A1 | 3/2003 | Amemiya et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0234369 A1 | 12/2003 | Glukhoy |
| 2004/0000650 A1 | 1/2004 | Yanagisawa et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |
| 2004/0232356 A1 | 11/2004 | Norimine et al. |
| 2004/0240626 A1 | 12/2004 | Moyers |
| 2005/0058245 A1 | 3/2005 | Ein-Gal |
| 2005/0089141 A1 | 4/2005 | Brown |
| 2005/0161618 A1 | 7/2005 | Pedroni |

(56) References Cited

U.S. PATENT DOCUMENTS

| | | |
|---|---|---|
| 2005/0184686 A1 | 8/2005 | Caporasco et al. |
| 2005/0228255 A1 | 10/2005 | Saracen et al. |
| 2005/0234327 A1 | 10/2005 | Saracen et al. |
| 2005/0247890 A1 | 11/2005 | Norimine et al. |
| 2006/0017015 A1 | 1/2006 | Sliski et al. |
| 2006/0067468 A1 | 3/2006 | Rietzel |
| 2006/0126792 A1 | 6/2006 | Li |
| 2006/0284562 A1 | 12/2006 | Hruby et al. |
| 2007/0001128 A1 | 1/2007 | Sliski et al. |
| 2007/0014654 A1 | 1/2007 | Haverfield et al. |
| 2007/0023699 A1 | 2/2007 | Yamashita et al. |
| 2007/0029510 A1 | 2/2007 | Hermann et al. |
| 2007/0051904 A1 | 3/2007 | Kaiser et al. |
| 2007/0092812 A1 | 4/2007 | Caporaso et al. |
| 2007/0145916 A1 | 6/2007 | Caporaso et al. |
| 2007/0171015 A1 | 7/2007 | Antaya |
| 2007/0181519 A1 | 8/2007 | Khoshnevis |
| 2007/0284548 A1 | 12/2007 | Kaiser et al. |
| 2008/0093567 A1 | 4/2008 | Gall |
| 2008/0218102 A1 | 9/2008 | Sliski |
| 2009/0096179 A1 | 4/2009 | Stark et al. |
| 2009/0140671 A1 | 6/2009 | O'Neal, et al. |
| 2009/0140672 A1 | 6/2009 | Gall et al. |
| 2009/0200483 A1 | 8/2009 | Gall et al. |
| 2011/0220809 A1 | 9/2011 | Yajima et al. |
| 2012/0126140 A1 | 5/2012 | Gall et al. |
| 2013/0237425 A1 | 9/2013 | Leigh et al. |
| 2014/0097920 A1 | 4/2014 | Goldie et al. |

FOREIGN PATENT DOCUMENTS

| | | |
|---|---|---|
| DE | 31 48 100 | 6/1983 |
| DE | 35 30 446 | 8/1984 |
| DE | 41 01 094 C1 | 5/1992 |
| DE | 4411171 | 10/1995 |
| EP | 0 194 728 | 9/1986 |
| EP | 0194728 | 9/1986 |
| EP | 0 277 521 | 8/1988 |
| EP | 0 208 163 | 1/1989 |
| EP | 0 222 786 | 7/1990 |
| EP | 0 221 987 | 1/1991 |
| EP | 0 499 253 | 8/1992 |
| EP | 0 306 966 | 4/1995 |
| EP | 0 388 123 | 5/1995 |
| EP | 0 465 597 | 5/1997 |
| EP | 0 911 064 | 6/1998 |
| EP | 0 864 337 | 9/1998 |
| EP | 0 776 595 | 12/1998 |
| EP | 1 069 809 | 1/2001 |
| EP | 1 153 398 | 4/2001 |
| EP | 1 294 445 | 3/2003 |
| EP | 1 348 465 | 10/2003 |
| EP | 1 358 908 | 11/2003 |
| EP | 1 371 390 | 12/2003 |
| EP | 1 402 923 | 3/2004 |
| EP | 1 430 932 | 6/2004 |
| EP | 1 454 653 | 9/2004 |
| EP | 1 454 654 | 9/2004 |
| EP | 1 454 655 | 9/2004 |
| EP | 1 454 656 | 9/2004 |
| EP | 1 454 657 | 9/2004 |
| EP | 1 477 206 | 11/2004 |
| EP | 1 738 798 | 1/2007 |
| EP | 1 826 778 | 8/2007 |
| EP | 1 949 404 | 7/2008 |
| EP | 2183753 | 7/2008 |
| EP | 2394498 | 2/2010 |
| EP | 2219732 | 8/2010 |
| EP | 1 605 742 | 6/2011 |
| FR | 2 560 421 | 8/1985 |
| FR | 2911843 | 8/2008 |
| GB | 957342 | 5/1964 |
| GB | 2 015 821 | 9/1979 |
| GB | 2 361 523 | 10/2001 |
| JP | 43-23267 | 10/1968 |
| JP | 48-108098 | 12/1973 |
| JP | 61-80800 | 4/1986 |
| JP | 62-150804 | 7/1987 |
| JP | 62-186500 | 8/1987 |
| JP | 10-071213 | 3/1988 |
| JP | 63-149344 | 6/1988 |
| JP | 63-218200 | 9/1988 |
| JP | 63-226899 | 9/1988 |
| JP | 01-276797 | 11/1989 |
| JP | 4-94198 | 3/1992 |
| JP | 04-128717 | 4/1992 |
| JP | 04-129768 | 4/1992 |
| JP | 04-273409 | 9/1992 |
| JP | 04-337300 | 11/1992 |
| JP | 05-341352 | 12/1993 |
| JP | 06-233831 | 8/1994 |
| JP | 06-036893 | 10/1994 |
| JP | 07-260939 | 10/1995 |
| JP | 08-173890 | 7/1996 |
| JP | 08-264298 | 10/1996 |
| JP | 09-162585 | 6/1997 |
| JP | 11-47287 | 2/1999 |
| JP | 11-102800 | 4/1999 |
| JP | 11-243295 | 9/1999 |
| JP | 2000-294399 | 10/2000 |
| JP | 2001-6900 | 1/2001 |
| JP | 2001-129103 | 5/2001 |
| JP | 2002-164686 | 6/2002 |
| JP | 2009-515671 | 4/2009 |
| JP | 2011-500152 | 1/2011 |
| JP | 5336499 | 8/2013 |
| SU | 300137 | 11/1969 |
| SU | 569 635 | 8/1977 |
| TW | 200930160 | 7/2009 |
| TW | 200934682 | 8/2009 |
| TW | 200939908 | 9/2009 |
| TW | 200940120 | 10/2009 |
| TW | I401176 | 7/2013 |
| WO | WO 86/07229 | 12/1986 |
| WO | WO 90/12413 | 10/1990 |
| WO | WO 92/03028 | 2/1992 |
| WO | WO 93/02536 | 2/1993 |
| WO | WO 98/17342 | 4/1998 |
| WO | WO 99/39385 | 8/1999 |
| WO | WO 00/40064 | 7/2000 |
| WO | WO 00/49624 | 8/2000 |
| WO | WO 01/26569 | 4/2001 |
| WO | WO 02/07817 | 1/2002 |
| WO | WO 03/039212 | 5/2003 |
| WO | WO 03/092812 | 11/2003 |
| WO | WO 2004/026401 | 4/2004 |
| WO | WO 2004/101070 | 11/2004 |
| WO | WO 2007/061937 | 5/2007 |
| WO | WO 2007/084701 | 7/2007 |
| WO | WO 2007/130164 | 11/2007 |
| WO | WO 2007/145906 | 12/2007 |
| WO | WO 2008/030911 | 3/2008 |
| WO | WO 2009/048745 | 4/2009 |
| WO | WO 2009/070173 | 6/2009 |
| WO | WO2009/070588 | 6/2009 |
| WO | WO2009/073480 | 6/2009 |

OTHER PUBLICATIONS

Office action and response history of U.S. Appl. No. 11/601,056 to Mar. 24, 2009.

U.S. Appl. No. 11/601,056, filed Nov. 17, 2006, including copy of application as filed (including pending claims), transaction history.

U.S. Appl. No. 60/738,404, filed Nov. 18, 2005, including copy of application as filed, transaction history.

PCT application No. PCT/US2006/44853, filed on Nov. 17, 2006, with Publication No. WO/2007/061937, including copy of application as filed, transaction history.

U.S. Appl. No. 10/949,734, filed Sep. 24, 2004, Patent No. 7,208,748, issued on Apr. 24, 2007, including copy of application as filed, transaction history and allowed claims.

U.S. Appl. No. 11/724,055, filed Mar. 14, 2007, including copy of application as filed (including pending claims), transaction history.

(56) References Cited

OTHER PUBLICATIONS

U.S. Appl. No. 11/371,622, filed Mar. 9, 2006, including copy of application as filed, transaction history and pending claims.
U.S. Appl. No. 60/590,088, filed Jul. 21, 2004, including copy of application as filed, transaction history.
U.S. Appl. No. 11/948,662, filed Nov. 30, 2007, including copy of application as filed, transaction history and pending claims.
U.S. Appl. No. 11/187,633, filed Jul. 21, 2005, including copy of application as filed, transaction history and pending claims.
U.S. Appl. No. 11/948,359, filed Nov. 30, 2007, including copy of application as filed (including pending claims), transaction history.
PCT application No. PCT/US2005/25942 filed on Jul. 21, 2005, with Publication No. WO/2006/012452, including copy of application as filed, transaction history.
U.S. Appl. No. 11/463,403, filed Aug. 9, 2006, including copy of application as filed (including pending claims), transaction history.
U.S. Appl. No. 11/517,490, filed Sep. 7, 2006, including copy of application as filed (including pending claims), transaction history.
U.S. Appl. No. 11/624,769, filed Jan. 19, 2007, including copy of application as filed (including pending claims), transaction history.
PCT application No. PCT/US2007/01506 filed on Jan. 19, 2007, with Publication No. WO/2007/084701, including copy of application as filed, transaction history.
PCT application No. PCT/US2007/01628 filed on Jan. 19, 2007, with Publication No. WO/2007/130164, including copy of application as filed, transaction history.
PCT application No. PCT/US2007/77693 filed on Sep. 6, 2007 with Publication No. WO/2007/77693, including copy of application as filed, transaction history.
PCT application No. PCT/US2008/077513, filed on Sep. 24, 2008, including copy of application as filed, transaction history.
PCT application No. PCT/US2008/084695 filed on Nov. 25, 2008, including copy of application as filed, transaction history.
PCT application No. PCT/US2008/084699 filed on Nov. 25, 2008, including copy of application as filed, transaction history.
U.S. Appl. No. 60/991,454, filed Nov. 30, 2007, including copy of application as filed, transaction history.
U.S. Appl. No. 12/275,103, filed Nov. 20, 2008, including copy of application as filed (including pending claims), transaction history.
PCT Appl. No. PCT/US2007/086109 filed on Nov. 30, 2007, including copy of application as filed, transaction history.
U.S. Appl. No. 60/850,565, filed Oct. 10, 2006, including copy of application as filed, transaction history.
PCT International Search report and Written Opinion of PCT application No. PCT/US2006/044853, mailed Oct. 5, 2007 (12 pages).
PCT International Preliminary Report on Patentability of corresponding PCT application No. PCT/US2006/044853, mailed May 29, 2008 (8 pages).
International Search Report dated Aug. 26, 2008 in PCT application No. PCT/US2007/086109 (6 pages).
Written Opinion dated Aug. 26, 2008 in PCT application No. PCT/US2007/086109 (6 pages).
International Search Report and Written Opinion for PCT application No. PCT/US2008/084695 mailed Jan. 26, 2009 (15 pages).
International Search Report and Written Opinion for PCT application No. PCT/US2007/001506 mailed Jul. 5, 2007, Publication No. WO2007/084701, Published Jul. 26, 2007 (14 pages).
International Preliminary Report on Patentability for PCT application No. PCT/US2007/001506 mailed Jul. 5, 2007 (15 pages).
International Search Report for PCT/US2007/001628 mailed Feb. 18, 2008 (4 pages).
Written Opinion for PCT/US2007/001628, mailed Feb. 18, 2008 (11 pages).
International Preliminary Report on Patentability for PCT/US2007/001628, mailed Apr. 22, 2008 (15 pages).
Abrosimov, N. K., et al, "1000MeV Proton Beam Therapy facility at Petersburg Nuclear Physics Institute Synchrocyclotron", Medical Radiology (Moscow) 32, 10 (1987) revised in Journal of Physics, Conference Series 41, pp. 424-432, Institute of Physics Publishing Limited, 2006.
Adachi, T., et. al. "A 150MeV FFAG Synchrotron with "Return-Yoke Free" Magent" *Proceedings of the 2001 Particle Accelerator Conference*, Chicago (2001).
Ageyev, A. I., et. al. "The IHEP Accelerating and Storage Complex (UNK) Status Report" *11th International Conference on High-Energy Accelerators*, pp. 60-70 (Jul. 7-11, 1980).
Agosteo, S., et. al. "Maze Design of a gantry room for proton therapy" *Nuclear Instruments & Methods in Physics Research*, Section A, 382, pp. 573-582 (1996).
Allardyce, B. W., et al., "Performance and Prospects of the Reconstructed CERN 600 MeV Synchrocyclotron" IEEE Transactions on Nuclear Science USA ns-24:(3), pp. 1631-1633 (Jun. 1977).
Alexeev, V. P., et. al. "R4 Design of Superconducting Magents for Proton Synchrotrons" *Proceedings of the Fifth International Cryogenic Engineering Conference*, pp. 531-533 (1974).
Amaldi, U. "Overview of the world landscape of Hadrontherapy and the projects of the TERA foundation" *Physica Medica, An International journal Devoted to the Applications of Physics to Medicine and Biology*, vol. XIV, Supplement 1 (Jul. 1998), *6th Workshop on Heavy Charged Particles in Biology and Medicine*, Instituto Scientific Europeo (ISE), Baveno, pp. 76-85 (Sep. 29-Oct. 1, 1997).
Amaldi, U., et. al. "The Italian project for a hadrontherapy centre" *Nuclear Instruments and Methods in Physics Research A*, 360, pp. 297-301 (1995).
"An Accelerated Collaboration Meets with Beaming Success", Lawrence Livermore National Laboratory, Apr. 12, 2006, S&TR, Livermore, California, pp. 1-3. http://www.linl.gov/str/April06/Canoraso.html.
Anferov, V., et. al. "The Indiana University Midwest Proton Radiation Institute" *Proceedings of the 2001 Particle Accelerator Conference*, Chicago, pp. 645-647 (2001).
Anferov, V., et. al. "Status of the Midwest Proton Radiotherapy Institute", *Proceedings of the 2003 Particle Accelerator Conference*, pp. 699-701 (2003).
Arduini, G., et. al. "Physical specifications of clinical proton beams from a synchrotron" *Med. Phys.* 23 (6), pp. 939-951 (Jun. 1996).
Beeckman, W., et. al. "Preliminary design of a reduced cost proton therapy facility using a compact, high field isochronous cyclotron" *Nuclear Instruments and Methods in Physics Reasearch* B56/57, pp. 1201-1204 (1991).
Bellomo, G., et al., "The Superconducting Cyclotron Program at Michigan State University" *Bulletin of the American Physical Society*, vol. 25, No. 7, pp. 767 (Sep. 1980).
Benedikt, M. And Carli, C. "Matching to Gantries for Medical Synchrotrons" *IEEE Proceedings of the 1997 Particle Accelerator Conference*, pp. 1379-1381 (1997).
Bieth, C., et. al. "A Very Compact Protontherapy Facility Based on an Extensive Use of High Temperature Superconductors (HTS)" *Cyclotrons and their Applications 1998*, Proceedings of the Fifteenth International Conference on Cyclotrons and their Applications, Caen, pp. 669-672 (Jun. 14-19, 1998).
Bigham, C.B. "Magnetic Trim Rods for Superconducting Cyclotrons," Nuclear Instruments and Methods (North-Holland Publishing Co.) 141 (1975), pp. 223-228.
Blackmore, E. W., et. al. "Operation of the Triumf Proton Therapy Facility" *IEEE Proceedings of the 1997 Particle Accelerator Conferenc*, vol. 3, pp. 3831-3833 (May 12-16, 1997).
Bloch, C. "The Midwest Proton Therapy Center" *Application of Accelerators in Research and Industry, Proceedings of the Fourteenth Int'l. Conf.,* Part Two, pp. 1253-1255 (Nov. 1996).
Blosser, H., et. al. "A Compact Superconducting Cyclotron for the Production of High Intensity Protons" *Proceedings of the 1997 Particle Accelerator Conference*, vol. 1, pp. 1054-1056 (May 12-16, 1997).
Blosser, H., et al., "Advances in Superconducting Cyclotrons at Michigan State University", Proceedings of the 11th International Conference on Cyclotrons and their Applications, pp. 157-167 (Oct. 1986), Tokyo.
Blosser, H., "Application of Superconductivity in Cyclotron Construction", *Ninth International Conference on Cyclotrons and their Applications*, pp. 147-157 (Sep. 1981).

(56) References Cited

OTHER PUBLICATIONS

Blosser, H. "Applications of Superconducting Cyclotrons" *Twelfth International Conference on Cyclotrons and Their Applications*, pp. 137-144 (May 8-12, 1989).

Blosser, H., et al., "Characteristics of a 400 (Q2/A) MeV Super-Conducting Heavy-Ion Cyclotron", Bulletin of the American Physical Society, p. 1026 (Oct. 1974).

Blosser, H. G. "Compact Superconducting Synchrocyclotron Systems for Proton Therapy" *Nuclear Instruments & Methods in Physics Research*, Section B40-41, Part II, pp. 1326-1330 (Apr. 1989).

Blosser, H.G., "Future Cyclotrons" AIP, *The Sixth International Cyclotron Conference*, pp. 16-32 (1972).

Blosser, H., et. al. "Medical Accelerator Projects at Michigan State Univ." *IEEE Proceedings of the 1989 Particle Accelerator Conference*, vol. 2, pp. 742-746 (Mar. 20-23, 1989).

Blosser, H.G., "Medical Cyclotrons", *Physics Today*, Special Issue Physical Review Centenary, pp. 70-73 (Oct. 1993).

Blosser, H., et al., "Preliminary Design Study Exploring Building Features Required for a Proton Therapy Facility for the Ontario Cancer Institute", MSUCL-760a (Mar. 1991).

Blosser, H., Present and Future Superconducting Cyclotrons, *Bulletin of the American Physical Society*, vol. 32, No. 2, p. 171 (Feb. 1987), Particle Accelerator Conference, Washington, D.C. 1987.

Blosser, H., et al., "Problems and Accomplishments of Superconducting Cyclotrons", Proceedings of the 14$^{th}$ International Conference, Cyclotrons and Their Applications, pp. 674-684 (Oct. 1995).

Blosser, H.G., "Program on the Coupled Superconducting Cyclotron Project", *Bulletin of the American Physical Society*, vol. 26, No. 4, p. 558 (Apr. 1981).

Blosser, H., et al., "Superconducting Cyclotron for Medical Application", *IEEE Transactions on Magnetics*, vol. 25, No. 2, pp. 1746-1754 (Mar. 1989).

Blosser, H.G., et al., "Superconducting Cyclotrons", Seventh International Conference on Cyclotrons and their Applications, pp. 584-594 (Aug. 19-22, 1975).

Blosser, H.G., "Superconducting Cyclotrons at Michigan State University", Nuclear Instruments & Methods in Physics Research, vol. B 24/25, part II, pp. 752-756 (1987).

Blosser, H. G. "Synchrocyclotron Improvement Programs" *IEEE Transactions on Nuclear Science USA*, vol. 16, No. 3, Part I, pp. 405-414 (Jun. 1969).

Blosser, H.G., "The Michigan State University Superconducting Cyclotron Program", Nuclear Science, vol. NS-26, No. 2, pp. 2040-2047 (Apr. 1979).

Botha, A. H., et. al. "A New Multidisciplinary Separated-Sector Cyclotron Facility" IEEE Transactions on Nuclear Science, vol. NS-24, No. 3, pp. 1118-1120 (1977).

Chichili, D.R., et al., "Fabrication of Nb3Sn Shell-Type Coils with Pre-Preg Ceramic Insulation," American Institute of Physics Conference Proceedings, AIP USA, No. 711, (XP-002436709, ISSN: 0094-243X), 2004, pp. 450-457.

Chong, C.Y., et al., Radiology Clinic North American 7, 3319 (1969).

Chu, et al. "Instrumentation for Treatment of Cancer Using Proton and Light-ion Beams" Review of Scientific Instruments, 64 (8), pp. 2055-2122 (Aug. 1993).

Cole, et. al. "Design and Application of a Proton Therapy Accelerator", Fermi National Accelerator Laboratory, IEEE, 1985.

Conradie, et. al. "Proposed New Facilities for Proton Therapy at iThemba Labs" Proceedings of EPAC, pp. 560-562 (2002).

Source Search Cites of U.S. and Foreign Patents/Published applications in the name of Mitsubishi Denki Kabushiki Kaisha and Containing the Keywords (Proton and Synchrocyclotron), 8 pages.

Coupland, . "High-field (5 T) pulsed superconducting dipole magnet" Proceedings of the Institution of Electrical Engineers, vol. 121, No. 7, pp. 771-778 (Jul. 1974).

Coutrakon, et. al. "A prototype beam delivery system for the proton medical accelerator at Loma Linda" Medical Physics, vol. 18(6), pp. 1093-1099 (Nov./Dec. 1991).

Coutrakon, G et al. "Proton Synchrotrons for Cancer Therapy" Application of Accelerators in Research and Industry—Sixteenth International Conf., American Institute of Physics, vol. 576, pp. 861-864 (Nov. 1-5, 2000).

"CPAC Highlights Its Proton Therapy Program at ESTRO Annual Meeting", TomoTherapy Incorporated, Sep. 18, 2008, Madison, Wisconsin, pp. 1-2.

Cuttone, G., "Applications of a Particle Accelerators in Medical Physics" Istituto Nazionale di Fisica Nucleare-Laboratori Nazionali del Sud, V.S. Sofia, 44 Cantania, Italy, Jan. 2010 (17 pages).

Dahl, P. "Superconducting Magnet System" American Institute of Physics, AIP Conference Proceedings, vol. 2, pp. 1329-1376 (1987-1988).

Dialog Search, Jan. 31, 2005 (18 pages).

Dugan, G. et al. "Tevatron Status" IEEE, Particle Accelerator Conference, Accelerator Science & Technology (1989), pp. 426-430.

Eickhoff, et al. "The Proposed Accelerator Facility for Light Ion Cancer Therapy in Heidelberg" Proceedings of the 1999 Particle Accelerator Conference, New York, pp. 2513-2515 (1999).

Enchevich, B. et al., "Minimizing Phase Losses in the 680 MeV Synchrocyclotron by Correcting the Accelerating Voltage Amplitude," *Atomnaya Energiya* 26:(3), pp. 315-316 (1969).

Endo, K., et. al., "Compact Proton and Carbon Ion Synchrotrons for Radiation Therapy" Proceedings of EPAC 2002, Paris France, pp. 2733-2735 (2002).

Flanz, et al., "Large Medical Gantries", 1995 Particle Accelerator Conference, Massachusetts General Hospital, pp. 1-5 (1995).

Flanz, et al., "The Northeast Proton Therapy Center at Massachusetts General Hospital", Fifth Workshop on Heavy Charge Particles in Biology and Medicine, GSI, Darmstadt (Aug. 1995).

Flanz, et. al. "Treating Patients with the NPTC Accelerator Based Proton Treatment Facility" Proceedings of the 2003 Particle Accelerator Conference (2003), pp. 690-693.

Flanz, et al., "Operation of a Cyclotron Based Proton Therapy Facility", Massachusetts General Hospital, Boston, MA 02114, pp. 1-4.

Flood, W. S. and Frazier, P. E. "The Wide-Band Driven RF System for the Berkeley 88-Inch Cyclotron" American Institute of Physics, Conference Proceedings., No. 9, 459-466 (1972).

Foster, G. W. and Kashikhin, V. S. "Superconducting Superferric Dipole Magent with Cold Iron Core for the VLHC" IEEE Transactions on Applied Superconductivity, vol. 12, No. 1, pp. 111-115 (Mar. 2002).

Friesel, D. L. et al. "Design and Construction Progress on the IUCF Midwest Proton Radiation Institute" Proceedings of EPAC 2002, pp. 2736-2738 (2002).

Fukumoto, "Cyclotron Versus Synchrotron for Proton Beam Therapy", KEK Prepr., No. 95-122, pp. 533-536 (1995).

Fukumoto, et. al., "A Proton Therapy Facility Plan" Cyclotrons and their Applications, Proceedings of the 13th International Conference, Vancouver, Canada, pp. 258-261 (Jul. 6-10, 1992).

Gordon, et. al. "Design Study for a Compact 200 MeV Cyclotron" AIP Conference Proceedings Sixth International Cyclotron Conference, No. 9, pp. 78-86 (1972).

Gordon, M. M., "Extraction Studies for a 250 MeV Superconducting Synchrocyclotron", Proceedings of the 1987 IEEE Particle Accelerator Conference: Accelerator Engineering and Technology, pp. 1255-1257 (1987).

Goto, A. et al., "Progress on the Sector Magnets for the Riken SRC," American Institute of Physics, CP600, Cyclotrons and Their Applications 2001, Sixteenth International Conference (2001), pp. 319-323.

Graffman, S., et al., Acta Radiol. Therapy Phys. Biol. 9, 1 (1970).

Graffman, et. al. "Proton radiotherapy with the Uppsala cyclotron. Experience and plans" Strahlentherapie, 161, No. 12, pp. 764-770 (1985).

Graffman, et. al. "Design Studies for a 200 MeV Proton Clinic for Radiotherapy" AIP Conference Proceedings: Cyclotrons—1972, No. 9, pp. 603-615 (1972).

Hede, Karyn, "Research Groups Promoting Proton Therapy Lite", Journal of the National Cancer Institute, vol. 98, No. 23, Dec. 6, 2006, pp. 1682-1684.

(56) References Cited

OTHER PUBLICATIONS

Heinz, . "Superconducting Pulsed Magnetic Systems for High-Energy Synchrotrons" *Proceedings of the Fourth International Cryogenic Engineering Conference*, pp. 55-63. (May 24-26, 1972).
Hentschel, R., et. al., "Plans for the German National Neutron Therapy Centre with a Hospital-Based 70 MeV Proton Cyclotron at University Hospital Essen/Germany" *Cyclotrons and their Applications, Proceedings of the Fifteenth International Conference on Cyclotrons and their Applications*, Caen, Franco, pp. 21-23 (Jun. 14-19, 1998).
Hepburn, et. al. "Superconducting Cyclotron Neutron Source for Therapy" *International Journal of Radiation Oncology Biology Physics*, vol. 3 complete, pp. 387-391 (1977).
Hirabayashi, H. "Development of Superconducting Magnets for Beam Lines and Accelerator at KEK" *IEEE Transaction on Magnetics*, vol. Mag-17, No. 1, pp. 728-731 (Jan. 1981).
"Indiana's mega-million proton therapy cancer center welcomes its first patients" [online] Press release, Health & Medicine Week, 2004, retrieved from NewsRx.com, Mar. 1, 2004, pp. 119-120.
Ishibashi, K. and McInturff, A., "Stress Analysis of Superconducting 10T Magnets for Synchrotron", Proceedings of the Ninth International Cryogenic Engineering Conference, pp. 513-516 (May 11-14, 1982).
Ishibashi, K. and McInturff, A. "Winding Design Study of Superconducting 10 T Dipoles for a Synchrotron" *IEEE Transactions on Magnetics*, vol. MAG-19, No. 3, pp. 1364-1367 (May 1983).
Jahnke, A., et. al. "First Superconducting Prototype Magnets for a Compact Synchrotron Radiation Source in Operation" *IEEE Transactions on Magnetics*, vol. 24, No. 2 (Mar. 1988), pp. 1230-1232.
Jones, D.T.L. "Progress with the 200 MeV Cyclotron Facility at the National Accelerator Centre" *Commission of the European Communities Radiation Protection Proceedings, Fifth Symposium on Neutron Dosimetry*, vol. II, pp. 989-998 (Sep. 17-21, 1984).
Jones, D. T. L. "Present Status and Future Trends of Heavy Particle Radiotherapy" *Cyclotrons and their Applications 1998, Proceedings of the Fifteenth International Conference on Cyclotrons and their Applications*, pp. 13-20 (Jun. 14-19, 1998).
Jones, and Dershem. "Synchrotron Radiation from Proton in a 20 TEV, 10 TESLA Superconducting Super Collider" *Proceedings of the 12th International Conference on High-Energy Accelerators*, pp. 138-140 (Aug. 11-16, 1983).
Jones, D. T. L. and Mills, S. J. "The South African National Accelerator Centre: Particle Therapy and Isotope Production Programmes" *Radiation Physics and Chemistry*, vol. 51, Nos. 4-6, pp. 571-578 (Apr.-Jun. 1998).
Jones, D. T. L., et. al. "Status Report of the NAC Particle Therapy Programme" *Stralentherapie and Onkologie*, vol. 175, Suppl. II, pp. 30-32 (Jun. 1999).
Jongen, Y., et. al. "Progress report on the IBA-SHI small cyclotron for cancer therapy" *Nuclear Instruments and Methods in Physics Research*, Section B, vol. 79, issue 1-4, pp. 885-889 (1993).
Jongen, Y., et. al. "The proton therapy system for MGH's NPTC: equipment description and progress report" *Bulletin du Cancer/Radiotherapie, Proceedings of the meeting of the European Heavy Particle Therapy Group*, vol. 83, Suppl. 1, pp. 219-222 (1996).
Jongen, Y., et. al. "Development of a Low-cost Compact Cyclotron System for Proton Therapy" *National Institute of Radiol. Sci.*, No. 81, pp. 189-200 (1991).
Jongen, Y. et. al. "The proton therapy system for the NPTC: equipment description and progress report" *Nuclear Instruments and methods in Physics Research*, Section B, vol. 113, No. 1, pp. 522-525 (1996).
Kanai, et al., "Three-dimensional Beam Scanning for Proton Therapy," Nuclear Instruments and Methods in Physic Research, Sep. 1, 1983, The Netherlands, vol. 214, No. 23, pp. 491-496.
Karlin, D.L., et al., "The State and Prospects in the Development of the Medical Proton Tract on the Synchrocyclotron in Gatchina", Med. Radiol., Moscow, vol. 28(3), pp. 28-32 (Mar. 1983)(German with English Abstract on end of p. 32).

Kats, M.M. And Druzhinin, B.L. "Comparison of Methods for Irradiation Prone Patients" *Atomic Energy*, vol. 94, No. 2, pp. 120-123 (Feb. 2003).
Kats, M. M. and Onosovskii, K. K. "a Planar Magnetooptical System for the Irradiation of a Lying Patient with a Proton Beam from Various Directions" *Instruments and Experimental Techniques*, vol. 39, No. 1, pp. 127-131 (1996).
Kats, M. M. and Onosovskii, K. K. "A Simple, Compact, Flat System for the Irradiation of a Lying Patient with a Proton Beam from Different Directions" *Instruments and Experimental Techniques*, vol. 39, No. 1, pp. 132-134 (1996).
Koehler, A.M., et al., "Range Modulators for Protons and Heavy Ions," *Nuclear Instruments and Methods*, vol. 131, pp. 437-440 (1975).
Khoroshkov, V. S., et. al. "Moscow Hospital-Based Proton Therapy Facility Design" *Am. Journal Clinical Oncology: CCT*, vol. 17, No. 2, pp. 109-114 (Apr. 1994).
Kim, J. and Yun, C. "A Light-Ion Superconducting Cyclotron System for Multi-Disciplinary Users" *Journal of the Korean Physical Society*, vol. 43, No. 3, pp. 325-331 (Sep. 2003).
Kim, J.W., "An Eight Tesla Superconducting Magnet for Cyclotron Studies," Ph.D. Dissertation, Michigan State University, Department of Physics and Astronomy (1994).
Kim, J , et al., "Construction of 8T Magnet Test Stand for Cyclotron Studies", *IEEE Transactions on Applied Superconductivity*, vol. 3, No. 1, pp. 266-268 (Mar. 1993).
Kim, J , et al., "Design Study of a Superconducting Cyclotron for Heavy Ion Therapy", *Cyclotrons and Their Applications 2001, Sixteenth International Conference*, pp. 324-326 (May 13-17, 2001).
Kim, J and Blosser, H., "Optimized Magnet for a 250 MeV Proton Radiotherapy Cyclotron", Cyclotrons and Their Applications 2001, *Sixteenth International Conference*, pp. 345-347 (May 2001).
Kim, J.W., et al., "Trim Coil System for the Riken Cyclotron Ring Cyclotron", *Proceedings of the 1997 Particle Accelerator Conference, IEEE*, vol. 3, pp. 214-235 (Dec. 1981). OR 3422-3424, 1998).
Kishida, N. and Yano, Y. "Beam Transport System for the RIKEN SSC (II)" *Scientific Papers of the Institute of Physical and Chemical Research*, vol. 75, No. 4, pp. 214-235 (Dec. 1981).
Koto, M. And Tsujii, H. "Future of Particle Therapy" *Japanese Journal of Cancer Clinics*, vol. 47, No. 1, pp. 95-98 (2001) [Lang.: Japanese], English abstract (http://sciencelinks.jp/j-east/article/200206/000020020601A05114534php).
Kraft, G. et al., "Hadrontherapy in Oncology", U. Amaldi and Lamson, editors Elsevier Science, 1994.
Krevet, et al, "Design of a Strongly Curved Superconducting Bending Magnet for a Compact Synchrotron Light Source", Advances in Cryogenic Engineering, vol. 33, pp. 25-32.
295 Larsson, B. "Biomedical Program for the Converted 200-MeV Synchrocyclotron at the Gustaf Werner Institute" *Radiation Research*, 104, pp. S310-S318 (1985).
Larsson, B., et al., Nature 182, 1222 (1958).
Lawrence, J.H., Cancer 10, 795 (1957).
Lawrence, J.H., et al., "Heavy particles in acromegaly and Cushing's Disease," in Endocrine and Norendocrine Hormone Producing Tumors (Year Book Medical Chicago, 1973), pp. 29-61.
Lawrence, J.H., et al., "Successful Treatment of Acromegaly: Metabolic and Clinical Studies in 145 Patients", The Journal of Clinical Endocrinology and Metabolism, vol. 31, No. 2, Aug. 1970.
Lawrence, J.H., et al., Treatment of Pituitary Tumors, (Excerpta medica, Amsterdam/American Elsevier, New York, 1973), pp. 253-262.
Lecroy, W., et al., "Viewing Probe for High Voltage Pulses", *Review of Scientific Instruments USA* 31(12), p. 1354 (Dec. 1960).
Linfoot, J.A., et al., "Acromegaly," in Hormonal Proteins and Peptides, edited by C.H. Li, (1975), pp. 191-246.
Literature Author and Keyword Search, Feb. 14, 2005 (44 pages).
Literature Author and Keyword Searches (Synchrotron), Jan. 25, 2005 (78 pages).
Literature Keyword Search, Jan. 24, 2005 (96 pages).
Literature Search, Jan. 26, 2005 (36 pages).
Literature Search and Keyword Search for Synchrocyclotron, Jan. 25, 2005 (68 pages).

(56) References Cited

OTHER PUBLICATIONS

Literature Search by Company Name/Component Source, Jan. 24, 2005 (111 pages).
Livingston, M. S., et. al. "A Capillary Ion Source for the Cyclotron" *Review Science Instruments*, vol. 10:63, pp. 63-67, (Feb. 1939).
"LLNL, UC Davis Team Up to Fight Cancer", Lawrence Livermore National Laboratory, Apr. 28, 2006, SF-06-04-02, Livermore, California, pp. 1-4.
Mandrillon, P. "High Energy Medical Accelerators" *EPAC 90, 2nd European Particle Accelerator Conference*, vol. 2, (Jun. 12-16, 1990), pp. 54-58.
Marti, F., et al., "High Intensity Operation of a Superconducting Cyclotron", *Proceedings of the 14the International Conference, Cyclotrons and Their Applications*, pp. 45-48 (Oct. 1995).
Martin, P. "Operational Experience with Superconducting Synchrotron Magnets" *Proceedings of the 1987 IEEE Particle Accelerator Conference*, vol. 3 of 3, pp. 1379-1382 (Mar. 16-19, 1987).
Meot, F., et. al. "ETOILE Hadrontherapy Project, Review of Design Studies" *Proceedings of EPAC 2002*, pp. 2745-2747 (2002).
Montelius, A., et. al. "The Narrow Proton Beam Therapy Unit at the Svedberg Laboratory in Uppsala" *ACTA Oncologica*, vol. 30, pp. 739-745 (1991).
Moser, H.O., et al., "Nonlinear Beam Optics with Real Fields in Compact Storage Rings", Nuclear Instruments & Methods in Physics Research/Section B, B30, Feb. 1988, No. 1, pp. 105-109.
National Cancer Institute Funding (Senate—Sep. 21, 1992) (www.thomas.loc.gov/cgi-bin/query/z!r102;S21SE2-712 (2 pages).
Nicholson, J. "Applications of Proton Beam Therapy" *Journal of the American Society of Radiologic Technologists*, vol. 67, No. 5, pp. 439-441 (May/Jun. 1996).
Nolen, J.A., et al., "The Integrated Cryogenic—Superconducting Beam Transport System Planned for MSU", *Proceedings of the 12th International Conference on High-Energy Accelerators*, pp. 549-551 (Aug. 1983).
Norimine, T., et. al. "A Design of a Rotating Gantry with Easy Steering for Proton Therapy" *Proceedings of EPAC 2002*, pp. 2751-2753 (2002).
Okumura, T., et. al. "Overview and Future Prospect of Proton Radiotherapy" *Japanese Journal of Cancer Clinics*, vol. 43, No. 2, pp. 209-214 (1997) [Lang.: Japanese].
Okumura, T., et. al. "Proton Radiotherapy" *Japanese Journal of Cancer and Chemotherapy*, 10. 20, No. 14, pp. 2149-2155 (1993) [Lang.: Japanese].
Outstanding from Search Reports, "Accelerator of Polarized Portons at Fermilab," 20 pages, 2005.
Palmer, R. and Tollestrup, A. V. "Superconducting Magnet Technology for Accelerators" *Annual Review of Nuclear and Particle Science*, vol. 34, pp. 247-284 (1984).
Patent Assignee and Keyword Searches for Synchrocyclotron, Jan. 25, 2005 (77 pages).
"Patent Assignee Search 'Paul Scharer Institute," Library Services at Fish & Richardson P.C., Mar. 20, 2007 (40 pages).
"Patent Prior Art Search for 'Proton Therapy System'," Library Services at Fish & Richardson P.C., Mar. 20, 2007 (46 pages).
Pavlovic, M. "Beam-optics study of the gantry beam delivery system for light-ion cancer therapy" *Nuclear Instruments and Methods in Physics Research*, Section A, vol. 399, No. 2, pp. 439-454(16) (Nov. 1997).
Pedroni, E. "Accelerators for Charged Particle Therapy: Performance Criteria from the User Point of View" *Cyclotrons and their Applications, Proceedings of the 13th International Conference*, pp. 226-233 (Jul. 6-10, 1992).
Pedroni, E. "Latest Developments in Proton Therapy" *Proceedings of EPAC 2000*, pp. 240-244 (2000).
Pedroni, E., et. al. "The 200-MeV proton therapy project at the Paul Scherrer Institute: Conceptual design and practical realization" *Medical Physics*, vol. 22, No. 1, pp. 37-53 (Jan. 1995).

Pedroni, E., et. al. "A Novel Gantry for Proton Therapy at the Paul Scherrer Institute" *Cycloctrons and Their Applications 2001: Sixteenth International Conference, AIP Conference Proceedings*, vol. 600, pp. 13-17 (2001).
Pedroni, E. and Enge, H. "Beam optics design of compact gantry for proton therapy" *Medical & Biological Engineering & Computing*, vol. 33, No. 3, pp. 271-277 (May 1995).
Pedroni, E. and Jermann, M. "SGSMP: Bulletin Mar. 2002 Proscan Project, Progress Report on the PROSCAN Project of PSI" [online] retrieved from www.sgsmp.ch/protA23.htrn, (5 pages) Mar. 2002.
Potts, R., et. al. "MPWP6-Therapy III: Treatment Aids and Techniques" *Medical Physics*, vol. 15, No. 5, p. 798 (Sep./Oct. 1988).
Pourrahimi, S. et al., "Powder Metallurgy Processed Nb3Sn(Ta) Wire for High Field NMR magnets," IEEE Transactions on Applied Superconductivity, vol. 5, No. 2, (Jun. 1995), pp. 1603-1606.
Prieels, D., et. al. "The IBA State-of-the-Art Proton Therapy System, Performances and Recent Results" *Application of Accelerators in Research and industry—Sixteenth Int'l. Conf, American Institute of Physics*, vol. 576, pp. 857-860 (Nov. 1-5, 2000).
Rabin, M. S. Z., et. al. "Compact Designs for Comprehensive Proton Beam Clinical Facilities" *Nuclear Instruments & Methods in Physics Research*, Section B, vol. 40-41, Part II, pp. 1335-1339 (Apr. 1989).
Research & Development Magazine, "Proton Therapy Center Nearing Completion", vol. 41, No. 9, Aug. 1999 (2 pages)(www.rdmag.com).
Resmini, F., "Design Characteristics of the K=800 Superconducting Cyclotron at M.S.U.", Cyclotron Laboratory, Michigan State University, East Lansing, Michigan 48824, IEEE Transaction on Nuclear Science, vol. NS-26, No. 2, Apr. 1979 (8 pages).
RetroSearch "Berkeley 88-Inch Cyclotron 'RF' or 'Frequency Control'," Jan. 21, 2005 (36 pages).
RetroSearch "Berkeley 88-Inch Cyclotron," Jan. 24, 2005 (170 pages).
RetroSearch "Bernard Gottschalk, Cyclotron, Beams, Compensated Upstream Modulator, Compensated Scatter," Jan. 21, 2005 (20 pages).
RetroSearch "Cyclotron with 'RF' or 'Frequency Control'," Jan. 21, 2005 (49 pages).
RetroSearch Gottschalk, Bernard, Harvard Cyclotron Wheel, Jan. 21, 2005 (20 pages).
RetroSearch "Loma Linda University, Beam Compensation Foil Wedge," Jan. 21, 2005 (15 pages).
RetroSearch "Loma Linda University Beam Compensation," Jan. 21, 2005 (60 pages).
Revised Patent Keyword Search, Jan. 25, 2005 (88 pages).
Rifuggiato, D., et. al. "Status Report of the LNS Superconducting Cyclotron" *Nukleonika*, vol. 48, pp. S131-S134 (Supplement 2, 2003).
Rode, C. H. "Tevatron Cryogenic System" *Proceedings of the 12th International Conference on High-energy Accelerators, Fermilab*, pp. 529-535 (Aug. 11-16, 1983).
Salzburger, H., et al., "Superconducting Synchrotron Magnets Supraleitende Synchrotronmagnete", Siemens A.G., Erlangen (West Germany). Abteilung Technische Physik, Report No. BMFT-FB-T-75-25, October 75, p. 147, Journal Announcement: GRAI7619; STAR1415, Subm-Sponsored by Bundesmin. Fuer Forsch. U. Technol. In German; English Summary.
Schillo, M., et. al. "Compact Superconducting 250 MeV Proton Cyclotron for the PSI Proscan Proton Therapy Project" *Cyclotrons and Their Applications 2001, Sixteenth International Conference*, pp. 37-39 (2001).
Schneider et al., "Superconducting Cyclotrons," IEEE Transactions on Magnetics, vol. MAG-11, No. 2, Mar. 1975, New York, pp. 443-446.
Schneider, R., et al., "Nevis Synchrocyclotron Conversion Program—RF System," *IEEE Transactions on Nuclear Science USA ns 16*(3) pp. 430-433 (Jun. 1969).
Schreuder, H.W. "Recent Developments in Superconducting Cyclotrons" *Proceedings of the 1995 Particle Accelerator Conference*, vol. 1, pp. 317-321 (May 1-5, 1995).
Schreuder, A. N., et. al. "The Non-orthogonal Fixed Beam Arrangement for the Second Proton Therapy Facility at the National Accelerator Centre" *Application of Accelerators in Research and Industry*,

(56) References Cited

OTHER PUBLICATIONS

*American Institute of Physics, Proceedings of the Fifteenth International Conference*, Part Two, pp. 963-966 (Nov. 1998).
Schubert, J. R. "Extending the Feasibility Boundary of the Isochronous Cyclotron" Dissertation submitted to Michigan State University, 1997, Abstract http://adsabs.harvard.edu/abs/1998PhDT.......147S.
Schubert, J. and Blosser, H. "Conceptual Design of a High Field Ultra-Compact Cyclotron for Nuclear Physics Research" *Proceedings of the 1997 Particle Accelerator Conference*, vol. 1, pp. 1060-1062 (May 12-16, 1997).
Shelaev, I. A., et. al. "Design Features of a Model Superconducting Synchrotron of JINR" *Proceedings of the 12th International Conference on High-energy Accelerators*, pp. 416-418 (Aug. 11-16, 1983).
Sisterson, J. M. "World Wide Proton Therapy Experience in 1997" *The American Insitute of Physics, Applications of Accelerators in Research and Industry, Proceedings of the Fifteenth International Conference*, Part Two, pp. 959-962 (Nov. 1998).
Sisterson, J. M. "Clinical Use of Proton and Ion Beams From a World-Wide Perspective" *Nuclear Instruments and Methods in Physics Research*, Section B, vols. 40-41, pp. 1350-1353 (1989).
Slater, J. M., et. al. "Development of a Hospital-Based Proton Beam Treatment Center" *International Journal of Radiation Oncology Biology Physics*, vol. 14, No. 4, pp. 761-775 (Apr. 1988).
Slater, J. M., et. al. "Developing a Clinical Proton Accelerator Facility: Consortium-Assisted Technology Transfer" *Conference Record of the 1991 IEEE Particle Accelerator Conference: Accelerator Science and Technology*, vol. 1, pp. 532-536 (May 6-9, 1991).
Smith, A., et. al. "The Northeast Proton Therapy Center at Massachusetts General Hospital" *Journal of Brachytherapy International*, pp. 137-139 (Jan. 1997).
Snyder, S. L. And Marti, F. "Central region design studies for a proposed 250 MeV proton cyclotron" *Nuclear Instruments and Methods in Physics Research*, Section A, vol. 355, pp. 618-623 (1995).
Soga, F. "Progress of Particle Therapy in Japan" *Application of Accelerators in Research and Industry, American Institute of Physics, Sixteenth International Conference*, pp. 869-872 (Nov. 2000).
Spiller, P., et. al. "The GSI Synchrotron Facility Proposal for Acceleration of High Intensity Ion and Proton Beams" *Proceedings of the 2003 Particle Accelerator Conference*, vol. 1, pp. 589-591 (May 12-16, 2003).
Stanford, A.L., et al., "Method of Temperature Control in Microwave Ferroelectric Measurements," Sperry Microwave Electronics Company, Clearwater, Florida, Sep. 19, 196 (1 page).
Superconducting Cyclotron Contract awarded by Paul Scherrer Institute (PSI), Villigen, Switzerland, http: //www.accel.de/News/superconducting_cyclotron_contract.html Feb. 3, 2005.
Takada, Yoshihisa Tsukumba, "A review of rotating gantries for heavy charged particle therapy," Symposium of Research Center for Charged Particle Therapy on Fundamental development of the charged particle therapy, Chiba (Japan), Nov. 13-14, 2001.
Takada, Y. "Conceptual Design of a Proton Rotating Gantry for Cancer Therapy" *Japanese Journal of Medical Physics*, vol. 15, No. 4, pp. 270-284 (1995).
Takayama, T., et al., "Compact Cyclotron for Proton Therapy," *Proceedings of the 8th Symposium on Accelerator Science and Technology*, Japan (Nov. 25-27, 1991) pp. 380-382.
Teng, L. C. "The Fermilab Tevatron" *Coral Gables 1981, Proceedings, Gauge Theories, Massive Neutrinos, and Proton Decay*, pp. 43-62 (1981).
"The Davis 76-Inch Isochronous Cyclotron", Beam on: Crocker Nuclear Laboratory, University of California.
"The K100 Neutron-therapy Cyclotron," National Superconducting Cyclotron Laboratory at Michigan State University (NSCL), retrieved from: http://www,nscl.msu.edu./tech/accelerators/k100, Feb. 2005

"The K250 Proton therapy Cyclotron," National Superconducting Cyclotron Laboratory at Michigan State University (NSCL), retrieved from: http://www.nscl.msu.edu/tech/accelerators/k25.html, Feb. 2005.
"The K250 Proton-therapy Cyclotron Photo Illustration," National Superconducting Cyclotron Laboratory at Michigan State University (NSCL), retrieved from: http://www.nscl.msu.edu/media/image/experimental-equipment-technology/250.html, Feb. 2005.
Tobias, C.A., et al., Cancer Research 18, 121 (1958).
Tom, J. L. "The Use of Compact Cyclotrons for Producing Fast Neutrons for Therapy in a Rotatable Isocentric Gantry" *IEEE Transaction on Nuclear Science*, vol. 26, No. 2, pp. 2294-2298 (Apr. 1979).
Toyoda, E., "Proton Therapy System", Sumitomo Heavy Industries, Ltd.
Trinks, U., et. al. "The Tritron: A Superconducting Separated-Orbit Cyclotron" *Nuclear Instruments and Methods in Physics Research*, Section A, vol. 244, pp. 273-282 (1986).
Tsuji, H. "The Future and Progress of Proton Beam Radiotherapy" *Journal of Japanese Society for Therapeutic Radiology and Oncology*, vol. 6, No. 2, pp. 63-76 (1994).
UC Davis School of Medicine, "Unlikely Partners Turn Military Defense into Cancer Offense", Current Issue Summer 2008, Sacramento, California, pp. 1-2.
Umezawa, M., et. al. "Beam Commissioning of the new Proton Therapy System for University of Tsukuba" *Proceedings of the 2001 Particle Accelerator Conference*, vol. 1, pp. 648-650 (Jun. 18-22, 2001).
van Steenbergen, A. "The CMS, a Cold Magnet Synchrotron to Upgrade the Proton Energy Range of the BNL Facility" *IEEE Transactions on Nuclear Science*, vol. 18, Issue 3, pp. 694-698 (Jun. 1971).
van Steenbergen, A. "Superconducting Synchroton Development at BNL" *Proceedings of the 8th International Conference on High-Energy Accelerators CERN 1971*, pp. 196-198 (1971).
Vandeplassche, D., et. al. "235 MeV Cyclotron for MGH's Northeast Proton Therapy Center (NPTC): Present Status" EPAC 96, *Fifth European Partical Accelerator Conference*, vol. 3, pp. 2650-2652 (Jun. 10-14, 1996).
Vorobiev, L.G., et al., "Concepts of a Compact Achromatic Proton Gantry with a Wide Scanning Field", Nuclear Instruments and Methods in Physics Research, Section A., vol. 406, No. 2, pp. 307-310 (1998).
Vrenken, H., et. al. "A Design of a Compact Gantry for Proton Therapy with 2D-Scanning" Nuclear Instruments and Methods in Physics Research, Section A, vol. 426, No. 2, pp. 618-624 (1999).
Wikipedia, "Cyclotron" http://en.wikipedia.org/wiki/Cyclotron (originally visited Oct. 6, 2005, revisited Jan. 28, 2009)(7 pages).
Wikipedia, "Synchrotron" http://en,wikipedia.org/wiki/Synchrotron (originally visited Oct. 6, 2005, revisited Jan. 28, 2009)(7 pages).
Worldwide Patent Assignee Search, Jan. 24, 2005 (224 pages).
Worldwide Patent Keyword Search, Jan. 24, 2005 (94 pages).
Wu, X., "Conceptual Design and Orbit Dynamics in a 250 MeV Superconducting Synchrocyclotron," Ph.D. Dissertation, Michigan State University, Department of Physics and Astronomy (1990).
York, R.C. et al., "Present Status and Future Possibilities at NSCL-MSU", EPAC 94, Fourth European Particle Accelerator Conference, pp. 554-556 (Jun. 1994).
York, R.C., et al., "The NSCL Coupled Cyclotron Project—Overview and Status", *Proceedings of the Fifteenth International Conference on Cyclotrons and their Applications*, pp. 687-691 (Jun. 1998).
Yudelev, M., et. al. "Hospital Based Superconducting Cyclotron for Neutron Therapy: Medical Physics Perspective" *Cyclotrons and their applications 2001, 16th International Conference. American Institute of Physics Conference Proceedings*, vol. 600, pp. 40-43 (May 13-17, 2001) http://www.osti.gov/energycitations/product.biblio.jsp?osti id=20468164 http://adsabs.harvard.edu/abs/2001AIPC..600...40Y http://scitation.aip.org/getabs/servlet/GetabsSevlet?prog=normal
&id=APCPS000600000000100040000001&idtype=cvips
&gifs=yes.
Zherbin, E. A., et al., "Proton Beam Therapy at the Leningrad Synchrocyclotron (Clinicomethodological Aspects and Therapeutic Results)", pp. 17-22, Aug. 1987, vol. 32(8)(German with English abstract on pp. 21-22).

(56) References Cited

OTHER PUBLICATIONS

"510(k) Summary: Ion Beam Applications S.A.", FDA, Apr. 13, 2001.
"510(k) Summary: Optivus Proton Beam Therapy System", Jul. 21, 2000, 5 pages.
European Search Report from application No. EP 06838033.6 (PCT/US2006/044853) mailed May 11, 2009 (69 pages).
European Patent Office communication for application No. 06838033.6, patent No. 1949404, mailed Aug. 5, 2009 (1 page).
Invitation to Pay Additional Fees and, where applicable, Protest Fees with partial search report for application No. PCT/US2008/077513 mailed Jul. 3, 2009 (62 pages).
Office action and response history of U.S. Appl. No. 11/601,056 to Aug. 24, 2009.
International Search Report and Written Opinion mailed Oct. 1, 2009 in PCT application No. PCT/US2008/077513 (73 pages).
Office action and response history of U.S. Appl. No. 11/601,056 up to Jan. 14, 2010.
English language Abstract for, and copy of, Appun, J. "Various problems of magnet fabrication for high-energy accelerators" Journal for All Engineers Interested in the Nuclear Field, pp. 10-16 (1967) [Lang.: German] with English bibliographic information (http://www.osti.gov/energycitations/product.biblio.jsp?osti_id=4442292), 11 pages.
Abrosimov, N. K. et al., "Neutron Time-of-Flight Spectrometer GNEIS at the Gatchina 1 GeV Proton Synchrocyclotron", Nuclear Instruments and Methods in Physics Research, NIMRD9 A242(1) 1-178 (1985), ISSN 0168-9002, Holland, Amsterdam, pp. 121-133, received Mar. 9, 1985 and revised form Jul. 31, 1985.
Blosser, H., et al, "Progress Toward an Experiment to Study the Effect of RF Grounding in an Internal Ion Source on Axial Oscillations of the Beam in a Cyclotron", National Superconducting Cyclotron Laboratory, Michigan State University, Report MSUCL-760, CP600, Cyclotrons and Their Applications 2001, Sixteenth International Conference, 2001 pp. 274-276.
C/E Source of Ions for Use in Sychro-Cyclotrons Search, Jan. 31, 2005, 9 pages.
Karlin, D.L., et al., "Medical Protonic Tract of Synchrocyclotron of the Leningrad Instituted of Nuclear Physics", Oct. 8, 1956, pp. 13-19 (English abstract on p. 19, last page).
Ogino, Takashi, "Heavy Charged Particle Radiotherapy-Proton Beam", Japanese Journal of Cancer and Chemotherapy vol. 30(13): pp. 2030-2035, Dec. 2003 English abstract on first page.
Office Communication from corresponding European Application No. 08836879.0 dated Jun. 23, 2010, 2 pages.
Response filed Jul. 29, 2010 from corresponding European Application No. 08836879.0 Office action issued Jun. 23, 2010, 14 pages.
International Preliminary Report on Patentability from corresponding PCT Application No. PCT/2008/077513 mailed Apr. 22, 2010, 11 pages.
Karlin, D.L., et al., "Medical Protonic Tract of Synchrocyclotron of the Leningrad Instituted of Nuclear Physics", Oct. 8, 1956, pp. 13-19 (English abstract on p. 19, last page.).
Miyamoto, S., et. al. "Development of the Proton Therapy System" *The Hitachi Hyoron*, vol. 79, 10, pp. 775-779 (1997) [Lang: Japanese], English abstract on first page (http://www.hitachi.com/rev/1998/revfeb98/rev4706.htm).
Ogino, Takashi, "Heavy Charged Particle Radiotherapy-Proton Beam", Japanese Journal of Cancer and Chemotherapy vol. 30(13): pp. 2030-2035, Dec. 2003, English abstract on second page.
Shintomi, T., et. al. "Technology and Materials for the Superconducting Super Collider (SSC) Project" [Lang.: Japanese], The Iron and Steel Institute of Japan 00211575, vol. 78, No. 8 (Aug. 1, 1992), pp. 1305-1313, http://ci.nii.ac.jp/naid/110001493249/en/, 1992, English abstact on first page.
Tadashi, I., et al., "Large superconducting super collider (SSC) in the planning and materials technology", vol. 78, No. 8 (Aug. 1, 1992), pp. 1305-1313, The Iron and Steel Institute of Japan 00211575, English abstract on first page.

The Journal of Practical Pharmacy, vol. 46, No. 1, 1995, pp. 97-103. [Japanese], English abstract on first page.
Tsuji, H., "Cancer Therapy by Proton Beam: Latest State and Future Prospects", *Isotope News*, No. 459, pp. 2-7 (1992), English abstract on first page.
Umegaki, K., et. al. "Development of an Advanced Proton Beam Therapy System for Cancer Treatment" *Hitachi Hyoron*, vol. 85, No. 9, pp. 605-608 (2003) [Lang.: Japanese], English abstract, http://www.hitachi.com/ICS Files/afieldfile/2004/06/01/r2003_04_104.pdf or http://www.hitachi.com/rev/archive/2003/2005649_12606.html (full text) [Hitachi, vol. 52, No. 4. Dec. 2003], English abstract on first page.
18th Japan Conference on Radiation and Radioisotopes [Japanese], Nov. 25-27, 1987, 9 pages, English abstract on first page.
Abrosimov, N.K., et al., "Neutron Time-of-Flight Spectrometer Gneis at the Gatchina GeV Proton Synchrocyclotron", Lemingrad Nuclear Physics Institute, Proc. Academy Science, USSR, 1985.
Appun, J. "Various problems of magnet fabrication for high-energy accelerators" Journal for All Engineers Interested in the Nuclear Field, pp. 10-16 (1967) [Lang.: German], English bibliographic information (http://www.osti.gov/energycitations/product.biblio.jsp?osti_id=4442292).
Blosser et al., "Progress toward an experiment to study the effect of RF grounding in an internal ion source on axial oscillations of the beam in a cyclotron," National Superconducting Cyclotron Laboratory, Michigan State University, Report MSUCL-760, CP600, Cyclotrons and their Applications 2011, Sixteenth International Conference, 2001, pp. 274-276.
C/E Source of Ions for Use in Sycho-Cyclotrons Search, Jan. 31, 2005, 9 pages.
Karlin, D.L., et al., "Medical Radiology" (Moscow) 28, 13 (1983).
Miyamoto, S., et al., "Development of the Proton Therapy System" The Hitachi Hyoron, vol. 79, 10, pp. 775-779 (1997) [Lang: Japanese], English abstract (http://www.hitachi.com/rev/1998/rev4706.htm).
Shintomi, T., et al., "Technology and Materials for the Superconducting Super Collider (SSC) Project"[Lang.: Japanese], The Iron and Steel Institute of Japan 00211575, vol. 78, No. 8 (Aug. 1, 1992), pp. 1305-1313, http://ci.nii.ac.jp/naid/110001493249/en/, 1992.
Tadashi, I., et al., "Large superconducting super collider (SSC) in the planning and materials technology", vol. 78, No. 8 (Aug. 1, 1992), pp. 1305-1313, The Iron and Steel Institute of Japan 00211575.
The Journal of Practical Pharmacy, vol. 46, No. 1, 1995, pp. 97-103, [Jananese].
Tsuji, H. "Cancer Therapy by Proton Beam: Latest State and Future Prospects", Isotope News, No. 459, pp. 2-7 (1992).
Umegaki, K., et al., "Development of an Advanced Proton Beam Therapy System for Cancer Treatment" Hitachi Hyoron, vol. 85, No. 9, pp. 605-608 (2003) [Lang.:Japanese], English abstract, http://www.hitachi.com/ICSFiles/afieldfile/2004/06/01/r2003_04_104.pdf or http://www.hitachi.com/rev/archive/2003/2005649_12606.html (full text) [Hitachi, vol. 52, No. 4 Dec. 2003].
18th Japan Conference on Radiation and Radioisotopes [Japanese], Nov. 25-27, 1987, 9 pages.
Chinese office action issued in Chinese application No. 200680051421.0 mailed Dec. 25, 2009 with English translation (19 pages).
Abrosimov, N.K., et al., "Neutron Time-of-Flight Spectrometer Gneis at the Gatchina1GeV Proton Synchrocyclotron", Lemingrad Nuclear Physics Institute, Proc. Academy Science, USSR, 1985.
Appun, J. "Various problems of magnet fabrication for the high-energy accelerators" Journal for All Engneers Interested in the Nuclear Field, pp. 10-16 (1967) [Lang.: German], English bibliographic information (http://www.osti.gov/energycitations/product.biblio.jsp?osti_id=4442292).
Blosser et al., "Progress toward an experiment to study the effect of RF Grounding in an internal ion source on axial oscillations of the beam in a cyclotron," National Superconducting Cyclotron Laboratory, Michigan State University, Report MSUCL-760, CP600, Cyclotrons and their Application 2011, Sixteenth International Conference, 2001, pp. 274-276.

(56) References Cited

OTHER PUBLICATIONS

Miyamoto, S. et al., "Development of the Proton Therapy System" The Hitachi Hyoron, vol. 79, 10, pp. 775-779 (1997) [Lang: Japanese], English abstract (http://www.hitachi.com/rev/1998/revfeb98/rev4706.htm).

Shintomi, T., et al., "Technology and Materials for the Superconducting Super Collider (SSC) Project"[Lang.: Japanese], The Iron and Steel Institute of Japan 00211575, vol. 78, No. 8 (19920801), pp. 1305-1313, http://ci.nii.ac.jp/naid/110001493249/en/, 1992.

Tadashi, I., et al., "Large superconducting super collider (SSC) in the planning and material technology", vol. 78, No. 8 (Aug. 1, 1992), pp. 1305-1313, The Iron and Steel Institute of Japan 00211575.

The Journal of Practical Pharmacy, vol., 46 No. 1, 1995, pp. 97-103 [Japanese].

Tsuji, H., "Cancer Therapy by Proton Beam: Latest State and Future Prospects", Isotope News, No. 459, pp. 2-7 (1992).

Umegaki, K., et al. "Development of an Advanced Proton Beam Therapy System for Cancer Treatment" Hitachi Hyoron, vol. 85, No. 9, pp. 605-608 (2003) [Lang.:Japanese], English abstract, http://www.hitachi.com/ICSFiles/afieldfile/2004/06/01/r2003_04_104.pdf or htp://hitachi.com/rev/archive/2003/2005649_12606.html (full text) [Hitachi, vol. 52, No. 4 Dec. 2003].

18th Japan Conference on Radiation and Radioisotopes [Japenese], November 25-27, 1987, 9 pages.

Chinese office action issued in Chinese application No. 20680051421.0 mailed Dec. 25, 2009 with English translation (19 pages).

Canadian Office Action from corresponding Canadian application 2702036 issued Sep. 29, 2014 (9 pages).

\* cited by examiner

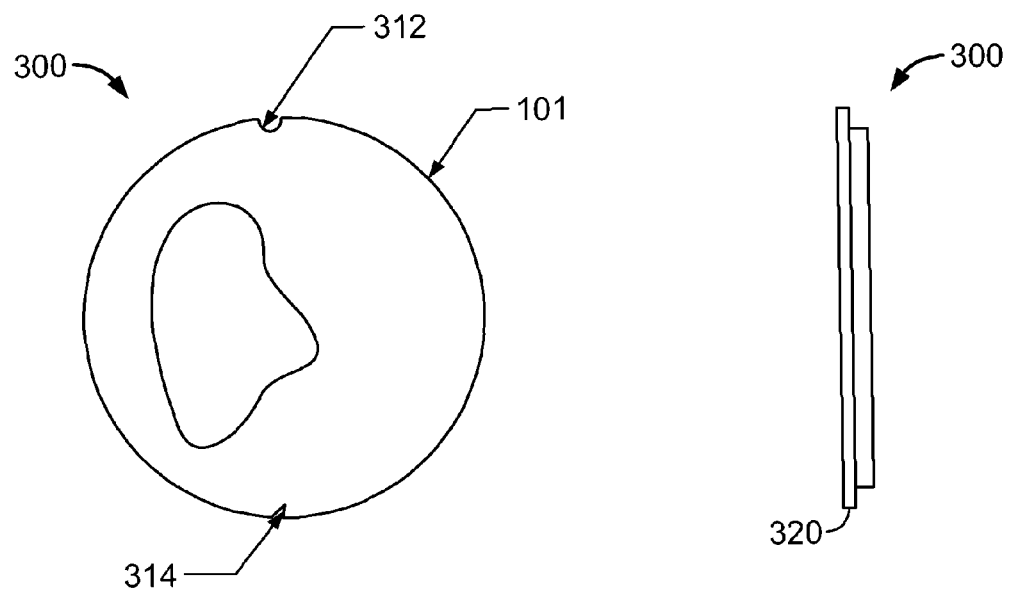
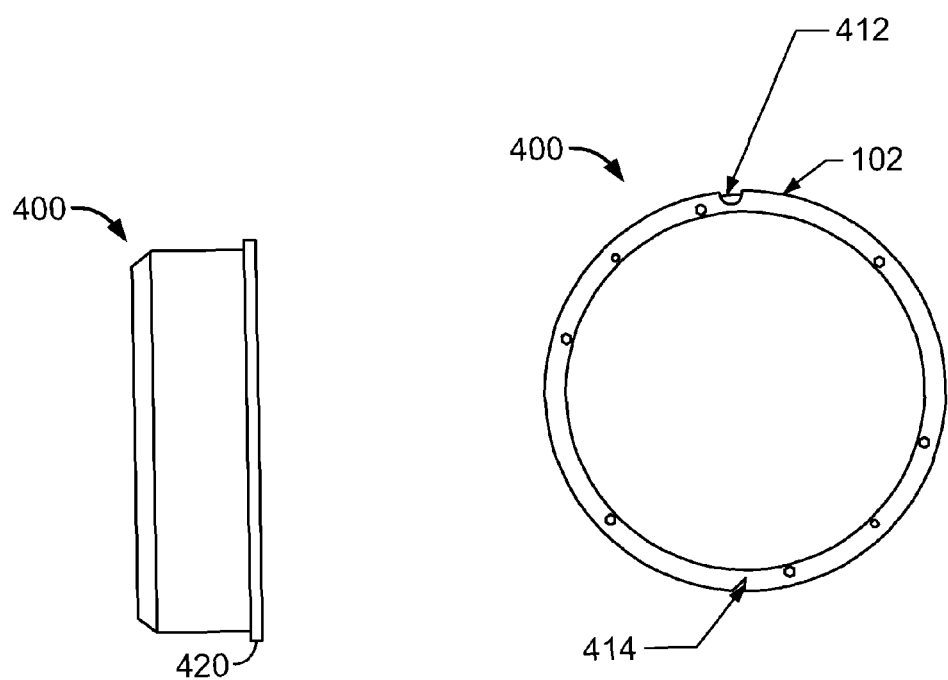

US 8,941,083 B2

APPLYING A PARTICLE BEAM TO A PATIENT

CLAIM OF PRIORITY

This application is a continuation and claims priority under 35 U.S.C. §120 to U.S. Pat. application Ser. No. 11/870,961, filed Oct. 11, 2007 now U.S. Pat. No. 8,003,964, the entire content is hereby incorporated by reference.

BACKGROUND

This description relates to applying a particle beam to a patient.

For therapy on a tumor, for example, a proton beam should be applied to all of the tumor and to none of the surrounding normal tissue, to the extent possible. An applicator can be placed across the therapy beam near the patient to help to control which tissue the proton beam reaches.

SUMMARY

Described herein is an apparatus comprising a yoke and a catch arm. The yoke comprises a first end and a second end, and is configured to hold a device comprising an aperture and a range compensation structure. The catch arm is pivotally secured to the first end of the yoke. The catch arm comprises a locking feature. The locking feature and the second end of the yoke interface, respectively, to a first retention feature and a second retention feature defined by the aperture and the range compensation structure. The locking feature is configured to interface to the first retention feature and the second end of the yoke is configured to interface to the second retention feature. The apparatus may comprise one or more of the following features, either alone or in combination.

The yoke may define a groove configured to receive a rim contained on the device. The second end of the yoke may comprise a pivot feature comprising a rounded protrusion and the first retention feature may comprise a notch on at least one of the aperture and the range compensation structure. The locking feature may comprise a hook and the second retention feature may comprise a notch on at least one of the aperture and the range compensation structure.

The apparatus may comprise a catch arm locking feature defined by the yoke to inhibit rotation of the catch arm. The catch arm locking feature may be for engaging a catch arm lock of the device. The catch arm lock may comprise a latch plate that is positionable to engage the catch arm locking feature. The catch arm locking feature may be configured to spring bias the latch plate.

The apparatus may comprise an indicator switch to detect locked and unlocked positions of the catch arm. At least one spring biased plunger may be on the yoke and may be configured to urge the device against the locking feature.

Also described herein is a method of loading a device onto a device holder. The method comprises positioning a first retention feature defined by the device so as to be received by a pivot feature defined by a yoke of the device holder, moving the device over the pivot feature and into the holder, and securing a second retention feature defined by the device with a locking feature defined by a catch arm pivotally secured to the yoke. The method may also comprise aligning a rim defined by the device with a groove defined by the yoke.

Also described herein is a proton applicator mount that comprises a base, a plurality of rollers associated with the base and configured to support a proton applicator, at least one alignment block associated with the base and configured to receive a corresponding alignment post of a proton applicator, and a locking clamp associated with the base. The locking clamp comprises a clamp bar, a handle attached to the clamp bar, a rotatable shaft carried by the base, and first and second hinges secured to the clamp bar and to the shaft. Each hinge comprises a hinge block defining a cam aperture and a cam path slot, a cam secured to the shaft and rotatably carried in the cam aperture of the hinge block, and a cam path protrusion on the base and configured to be received by the cam path slot. The cam aperture and the cam path slot are for guiding rotational and radial movement of the hinge block about the shaft. The proton applicator mount may also comprise one or more of the following features, either alone or in combination.

The cam may define a limit feature configured to be received by a corresponding cam aperture limit feature defined by the hinge block to limit rotation of the cam. The clamp bar may comprise at least one alignment block configured to receive a corresponding alignment post of the proton applicator.

The proton applicator mount may comprise a dovetail feature on the base and configured to align the proton applicator. The alignment block may define a substantially V-shaped groove. The alignment block may define a substantially conical receptacle. The handle may comprise a latch configured to be received by a latch receiver disposed on the base. Each cam of the first and second hinges may be spring biased.

Also described herein is a transport cart for a proton applicator. The transport cart comprises a cart body, a plurality of rollers disposed on an upper portion of the cart body and configured to support a proton applicator, at least one docking interlock comprising a docking protrusion extending outwardly from the cart body and configured to be received by a docking plate disposed on a docking target, a docking cam pivotally attached to the docking protrusion and configured to engage the docking plate to retain the cart against the docking target, and at least one applicator interlock comprising a locking cam pivotally attached to the upper portion of the cart body and spring biased to a locking position, the locking cam being configured to retain a proton applicator.

Also described herein is a method of loading a proton applicator onto a radiation beam delivery system. The method comprises docking a transport cart carrying the proton applicator against the radiation beam delivery system. At least one docking interlock of the transport cart engages and retains the transport cart against the radiation beam delivery system. The docking interlock comprises a docking protrusion extending outwardly from the cart body and configured to be received by a docking plate disposed on the radiation beam delivery system, and a docking cam pivotally attached to the docking protrusion and configured to engage the docking plate to retain the cart against the radiation beam delivery system. The method also comprises moving the proton applicator over a plurality cart rollers supporting the proton applicator and disposed on the transport cart across onto a plurality mount rollers disposed on a proton applicator mount of the radiation beam delivery system. The method may comprise one or more of the following features, either alone or in combination.

The method may comprise disengaging an applicator interlock disposed on the cart before moving the proton applicator. The applicator interlock may comprise a locking cam pivotally attached to the cart and configured to retain the proton applicator. The method may comprise engaging a locking clamp disposed on a base of the proton applicator mount after receiving the proton applicator. The locking clamp may comprise a clamp bar, a handle attached to the clamp bar, a rotatable shaft carried by the base, and first and second hinges secured to the clamp bar and the shaft. Each hinge may comprise a hinge block defining a cam aperture and a cam path slot, a cam secured to the shaft and rotatably carried in the cam aperture of a corresponding hinge block, and a cam path protrusion disposed on the base and configured to be received by the cam path slot. The cam aperture and the cam path slot are for guiding rotational and radial movement of the hinge block about the shaft.

These and other features and aspects and combinations of them can be expressed as methods, apparatus, systems, and means for performing functions and in other ways. Any of the foregoing features may be combined to form embodiments not specifically described herein.

Other features and advantages will be apparent from the description and the claims.

DESCRIPTION OF THE DRAWINGS

FIG. 7 is a top view of a patient aperture.

FIG. 8 is a side view of a patient aperture.

FIG. 9 is a side view of a range compensator.

FIG. 10 is a top view of a range compensator.

DETAILED DESCRIPTION

A proton applicator system (PAS) provides final collimation and range compensation of a proton beam to a clinical target, such as tumor, within a patient. The PAS can also shield other patient tissues from radiation intended for the target.

Figure 1:
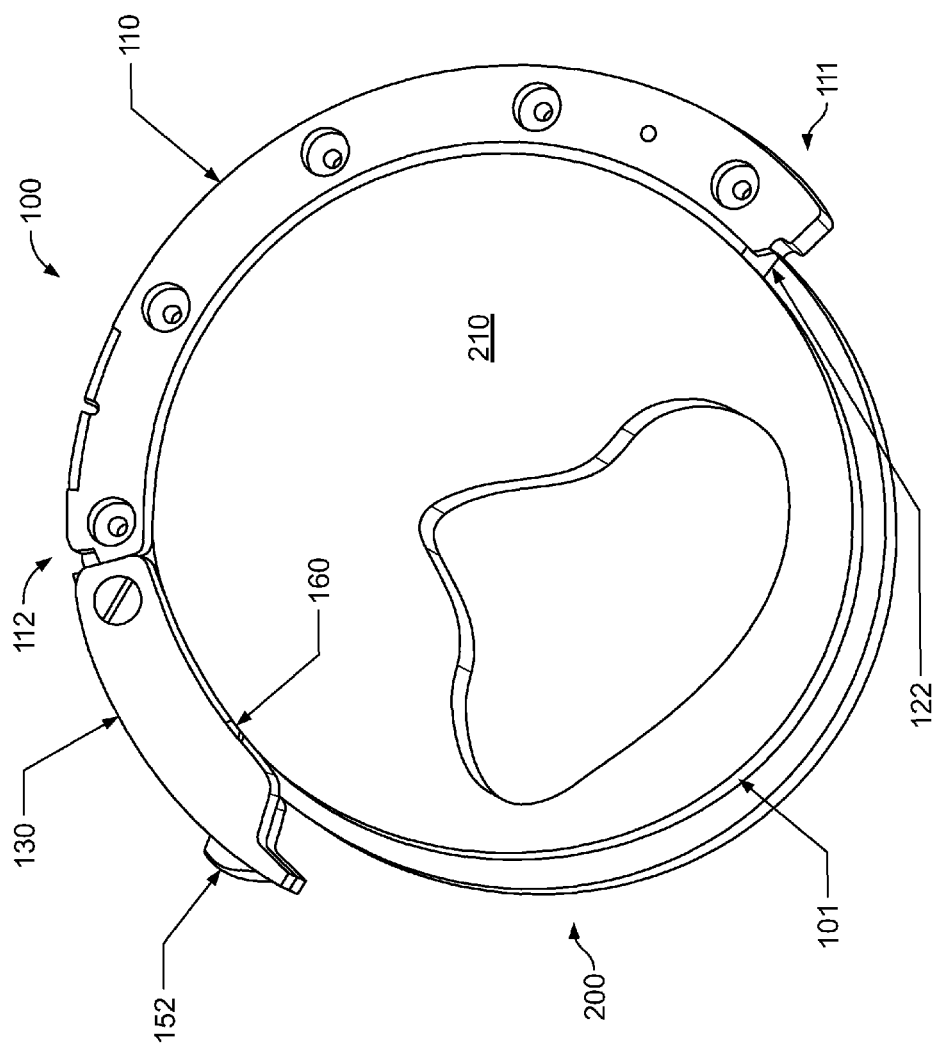
FIGS. 1 through 5 are perspective views of a holder.
Figure 2:
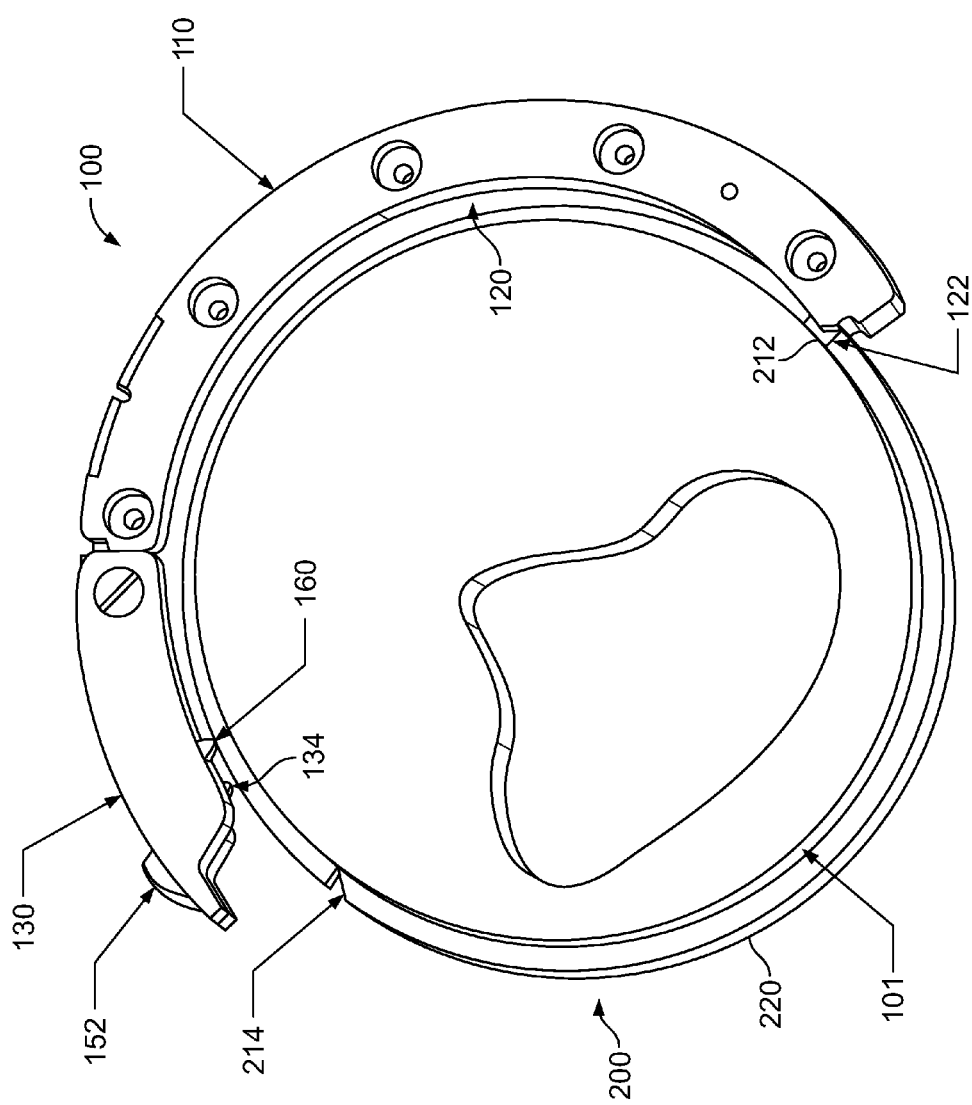
Figure 3:
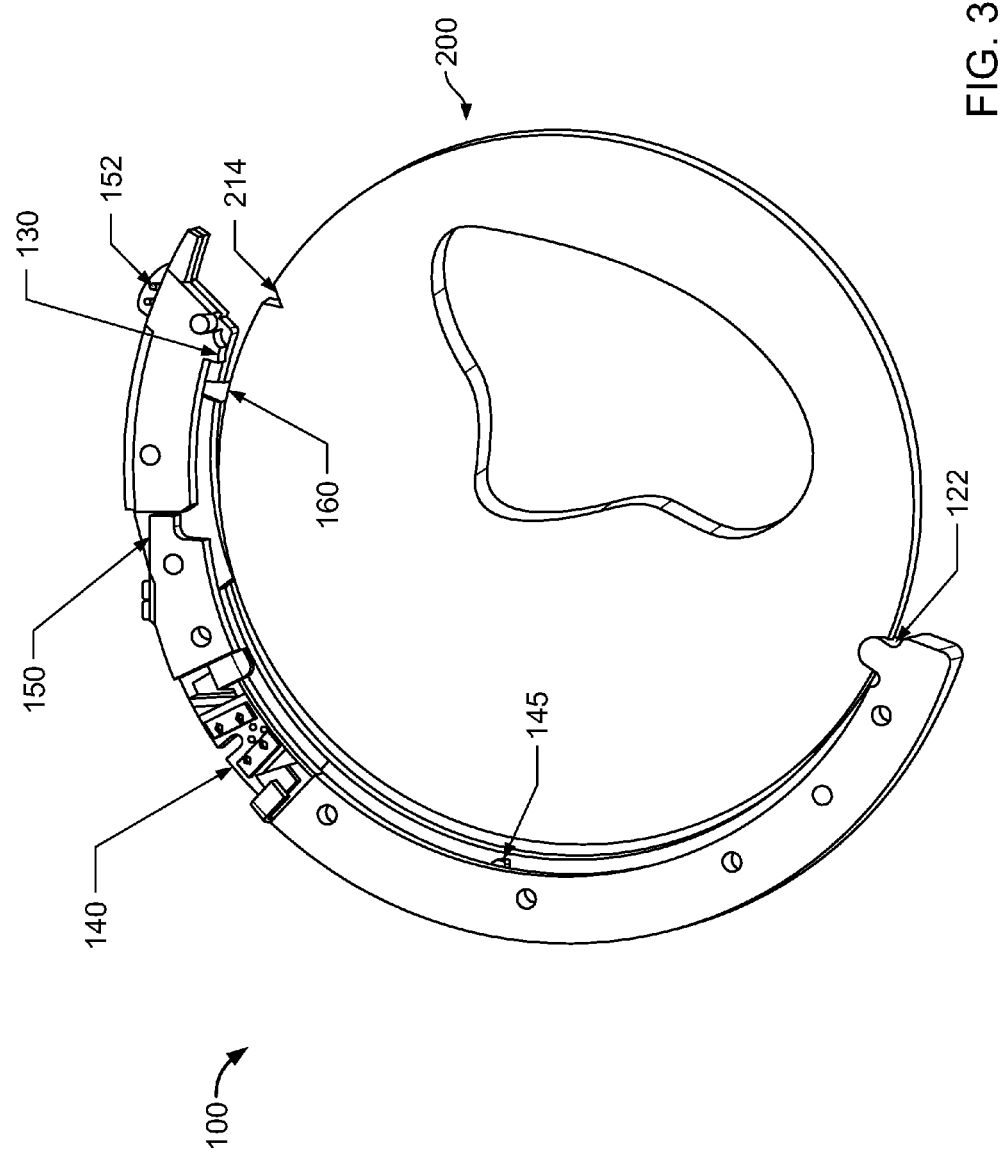

Referring to FIGS. 1-3, a holder 100 holds a device 200 that is part of a proton applicator system (e.g. a patient aperture and a range compensator) in a loaded position. A patient aperture may be used to limit the extent of application of a proton beam to patient tissue. A range compensator may be used to provide vertical compensation (e.g., height) relative to the patient tissue for the proton applicator. The holder 100 includes a main yoke piece 110 having first and second ends 111 and 112, respectively, and a pivot feature 122 (e.g., a protrusion) on the stationary yoke 110. The stationary yoke 110 may be arc-shaped or any other shape. The pivot feature 122 may include a rounded protrusion located near the first end 111 of the stationary yoke 110.

The device 200 includes a device body 210 defining first and second retention features 212 and 214, respectively. The first and second retention features 212, 214 may include notches that are defined by the device body 210. The pivot feature 122 may be configured to receive the first retention feature 212 of the device 200. The device 200 is pivoted over the pivot feature 122 into the holder 100. The holder 100 includes a locking catch 130 pivotally attached to the second end 112 of the stationary yoke 110 and a locking feature 134 (e.g., a hook) to receive the second retention feature 214 of the device 200, thereby retaining the device 200 in the holder 100. The locking catch 130 may be spring-biased toward a locking position with a spring 136. The device 200 may be held in the holder 100 axially by an associated rim 220 received by a groove 120 defined by the stationary yoke 110. The shape and size of the retention features 212, 214, the pivot feature 122, and locking feature 134 are scalable with outer dimensions of the device 200.

Referring to FIG. 3, the holder 100 includes an indicator switch 140 to detect a presence of the device 200 and the locked or unlocked positions of the catch 130. Spring-loaded plungers 145 on the holder 100 aid ejection of the device 200 upon release of the locking catch 130. The spring-loaded plungers 145 also keep the device 200 against the pivot feature 122. Locking feature 134 is arranged to reduce movement or tolerance jitter, which in turn makes for repeatable insertion of device 200 into the holder. The holder 100 may remain accurate and repeatable for hundreds of cycles.

Figure 4:
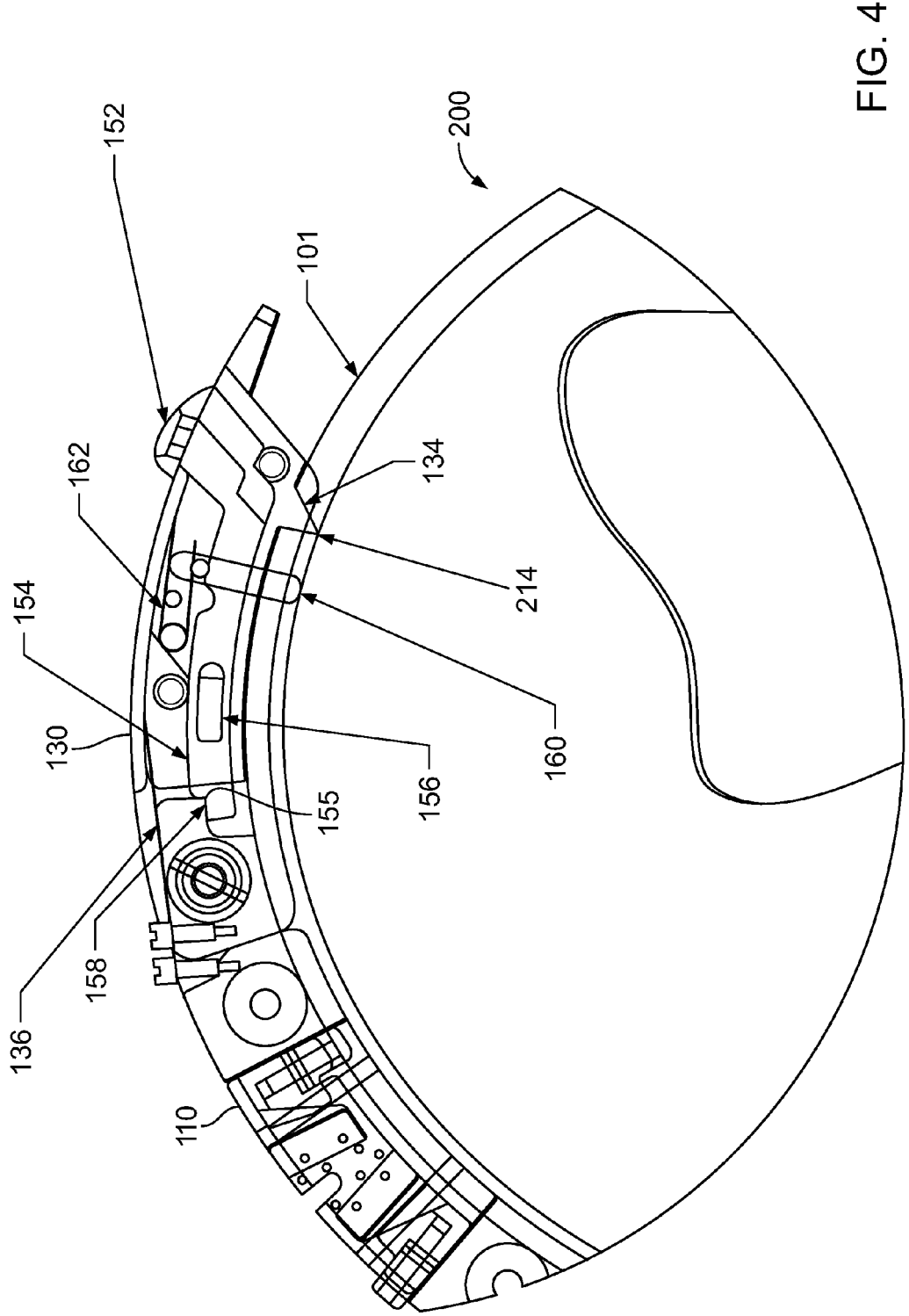
Figure 5:
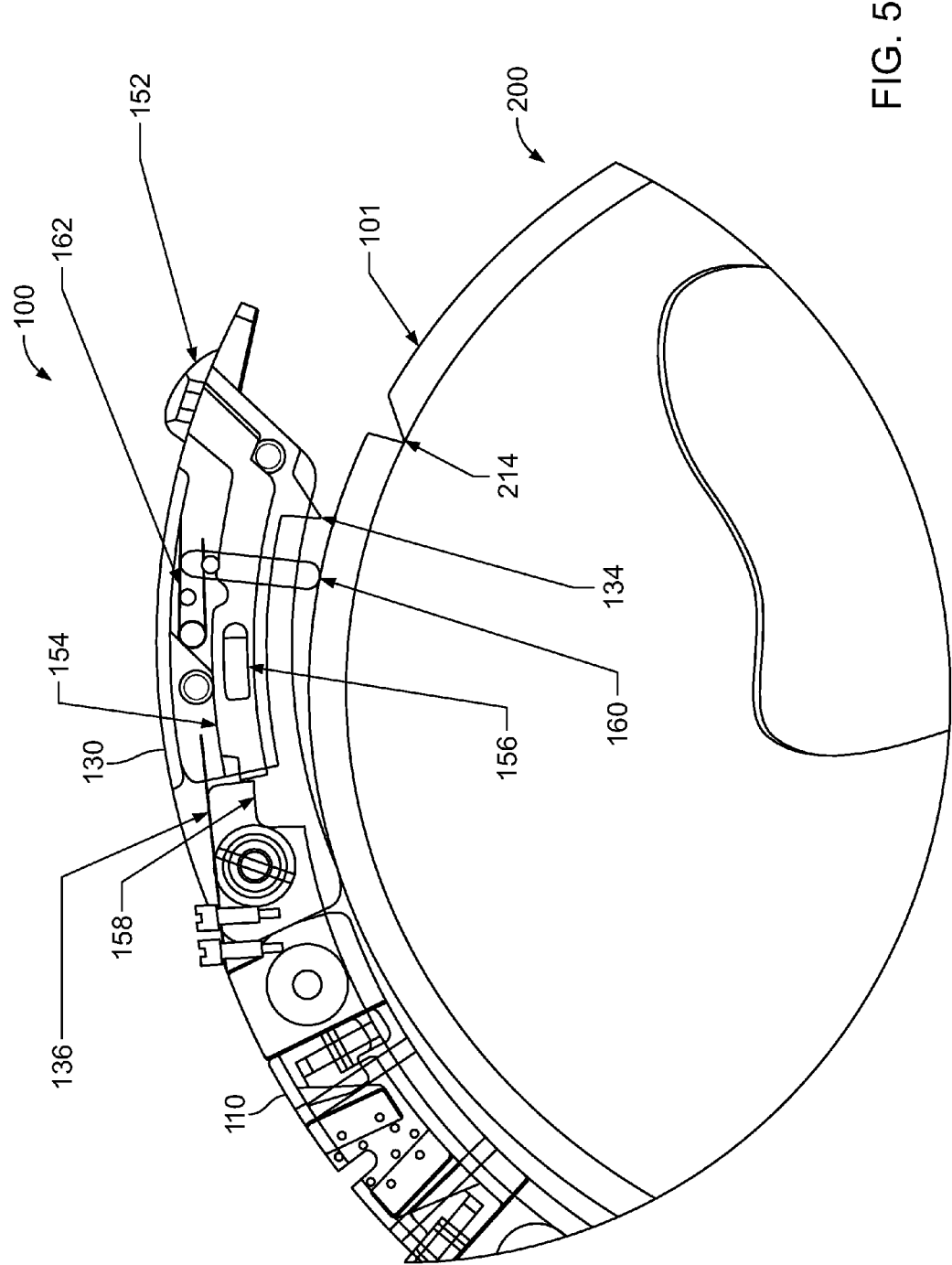
Figure 6:
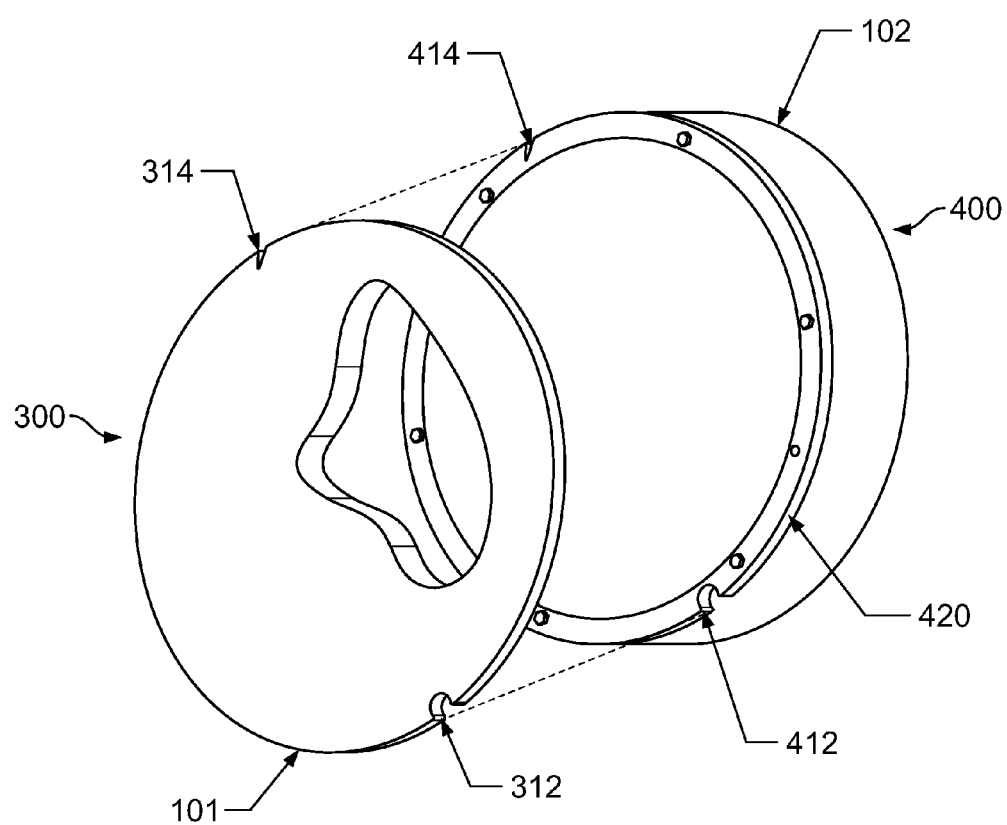
FIG. 6 is a perspective view of a patient aperture and range compensator assembly.

Referring to FIGS. 4 and 5, the holder 100 includes a secondary locking mechanism 150. FIG. 4 illustrates holder 100 in the locked position and FIG. 5 illustrates the holder 100 in the unlocked position. In this example, a user activates a secondary release button 152 and slightly rotates the locking catch 130 to release the device 200 from the holder 100. A latch plate 154 connected to the secondary release button 152 and the locking catch 130 is loaded in the locked position with a compression spring 156. The latch plate 154 locks the catch 130 in the loaded position by toggling into a recess 158 defined by the stationary yoke 110. When the secondary release button 152 and latch plate 154 are pulled forward, a secondary release linkage plunger 160 is moved into a detent 155 defined by the latch plate 154, thereby locking the latch plate 154 in a forward position, and allowing rotation of the locking catch 130. The secondary release linkage plunger 160 is biased by a spring 162 toward the detent 155. The device 200 can be safely removed manually.

As the device 200 is inserted into the holder 100 by placing the first retention feature 212 of the device 200 on the pivot feature 122 and rotating the device 200 into the holder 100, the locking catch 130 pivots or rotates into the second retention feature 214 of the device 200 to retain the device 200. As the device 200 rotates into the holder 100, the secondary release linkage plunger 160 is actuated up into the catch 130, allowing the latch plate 154 to lock into the recess 158 defined by the stationary yoke 110. The locked latch plate 154 reduces the chances that the catch 130 will inadvertently rotate outward and release the device 200.

Referring to FIGS. 6-10, multiple holders 100 may be layered or stacked to allow for various device thicknesses and weight ranges. Example of devices that the holder 100 can lock and retain include both a patient aperture 300 and a range compensator 400. The aperture 300 includes an aperture body 310 defining first and second retention features 312 and 314, repetitively. The range compensator 400 includes a range compensator body 410 defining first and second retention features 412 and 414, repetitively. The aperture 300 and the range compensator 400 are each held in lateral and longitudinal directions by the first and second retention features 312, 314, 412, and 414. The first retention features 312 and 412 are configured to engage and be received by the pivot feature 122 disposed on the holder 100. The second retention features 314 and 414 are configured to be received by the locking feature 134 of the catch 130. Both devices 300 and 400 are individually loaded and retained by the same features 122, 134 of the holder 100. The patient aperture 300 and the range compensator 400 both include a retention edge or rim 320 and 420, respectively, configured to be received by the groove 120 defined by the stationary yoke 110 for axial retention.

Figure 11:
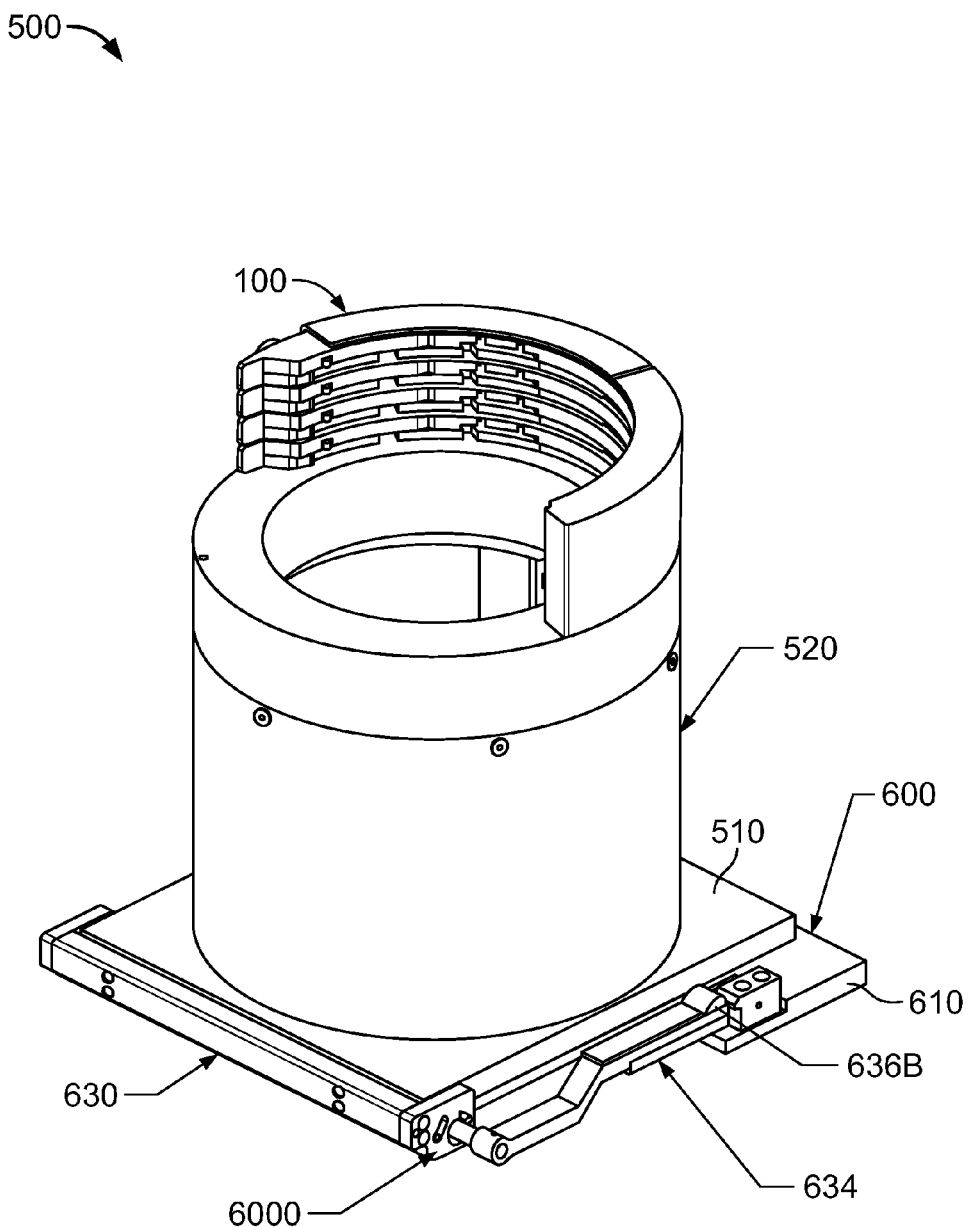
FIG. 11 is a perspective view of an applicator and an applicator mount system.
Figure 12:
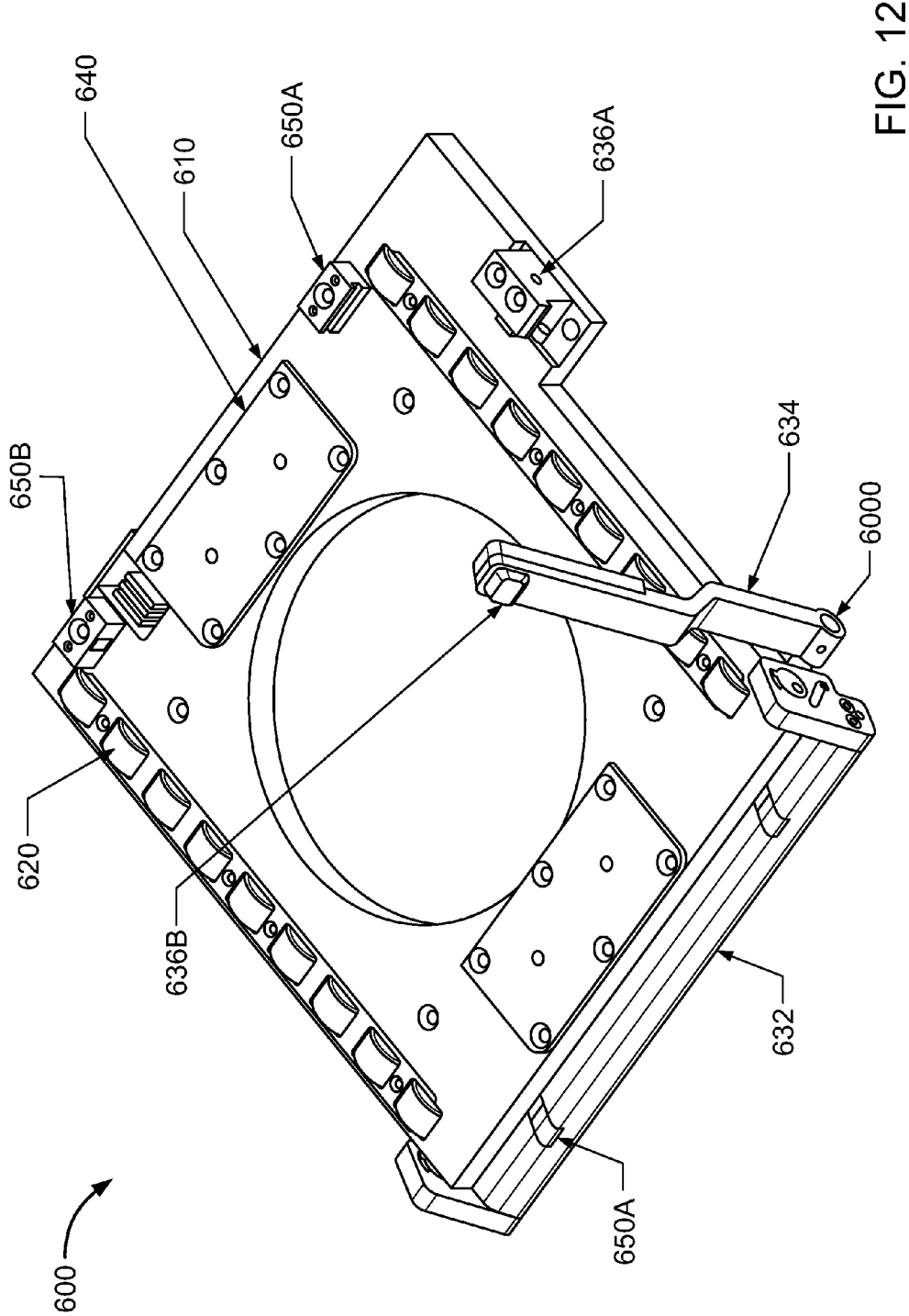
FIG. 12 is a perspective view of an applicator mount system.

Referring to FIGS. 11-12, in this example, a proton applicator 500 includes an applicator base 510 and assembly applicator 520, which may be secured to the base 510. One or more holders, such as those described above, may be secured to the assembly applicator 520. In the example shown in FIG. 11, four holders 100 are stacked and secured on the assembly applicator 510. An applicator mount system 600 is used to mount the proton applicator 500 to a C-Inner Gantry (not shown). The applicator mount system 600 includes a base 610, a plurality of rollers 620 carried by the base 610 and exposed at a top surface 612 of the base 610, and an eccentric locking clamp (clamping bar) 630. The locking clamp holds the applicator in place during transport. When the locking clamp 630 is lowered, the applicator 500 may be rolled onto the applicator mount system 600 from an applicator transport cart 700 (see FIG. 18). As the applicator 500 is transferred from the cart 700 to the mount system 600, it is captured by dovetail features 640 on the base 610. The dovetail features 640 allow for course alignment and axial retention of the applicator 500. After the applicator 500 moves to the end of its travel, it comes to rest on stationary tooling ball alignment blocks 650 secured on the base 610.

Figure 13:
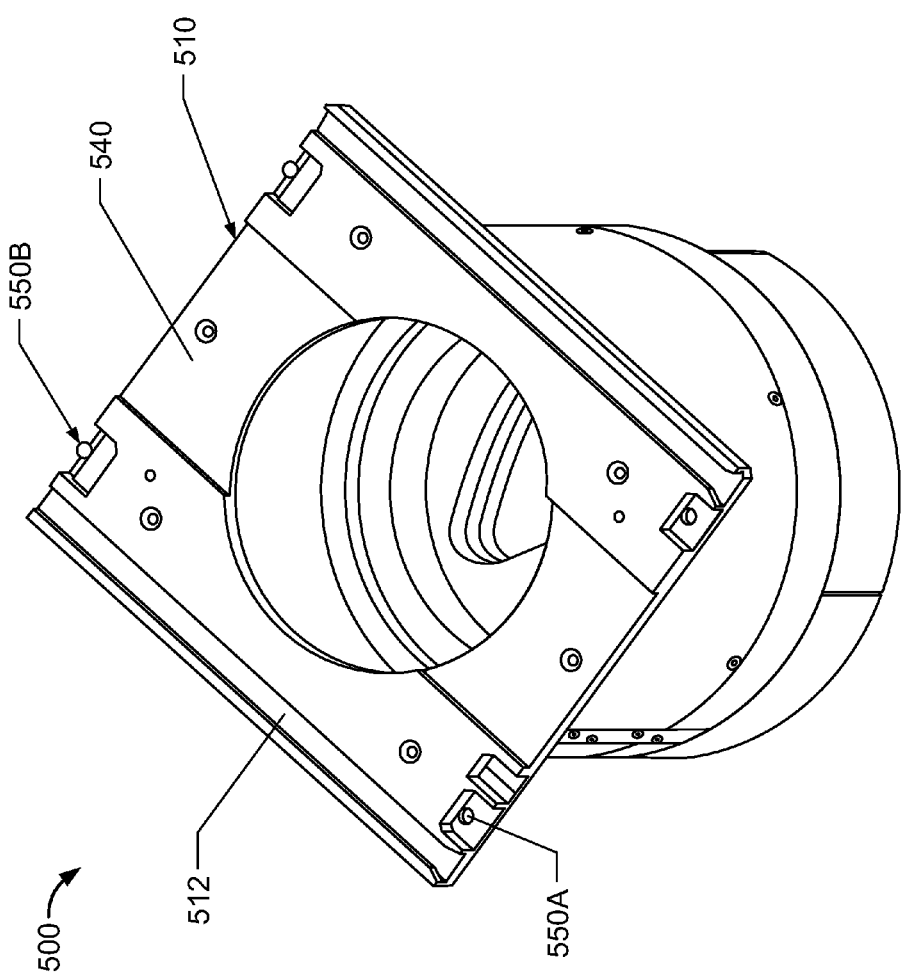
FIG. 13 is a bottom perspective view of a proton applicator.

Referring to FIGS. 12-13, the alignment blocks 650 are configured to interface with the tooling ball posts 550A (e.g., tooling balls) located on the applicator base 510. Two types of tooling ball alignment blocks 650 are mounted on the mount system base 610, a V-groove alignment block 650A defining a V-groove, and a cone alignment block 650B defining a conical receptacle. The V-groove alignment block 650A restrains the applicator 500 axially and the cone alignment block 650B positions and restrains the applicator 500 perpendicular to a load direction and axially. Both alignment blocks 650A, 650B act to restrain or position the applicator 500 in the load direction. The applicator base 510 defines a dovetail groove 540 configured to mate with the dovetail features 640 on the mount system base 610. The applicator base 510 defines roller grooves 512 configured to receive the mount system base rollers 620.

The eccentric locking clamp 630 is located on the opposite end of the mount system base 610 from the alignment blocks 650. The eccentric locking clamp 630 includes a clamping bar 632, a pair of V-groove alignment blocks 650A disposed on the clamping bar 632, a lock handle 634 connected to the clamping bar 632, and eccentric hinges 6000. The lock handle 634 (FIG. 16) includes a secondary release latch 636, which includes a secondary release block 636A secured to the base 610 and configured to retain a secondary release button 636B on the lock handle 634. When actuated, the eccentric locking clamp 630 imparts a clamping force onto the applicator base 510, locking the applicator 500 onto the applicator mount system 600. The eccentric hinging action of the locking clamp 630 has a rotational component that brings the clamp bar 632 into position against spring loaded tooling balls 550B on a side of the applicator base 510. The eccentric hinging action of the locking clamp 630 also has linear component that drives the clamp bar 632 and V-groove alignment blocks 650A forward to lock the applicator 500 into position.

Figure 14:
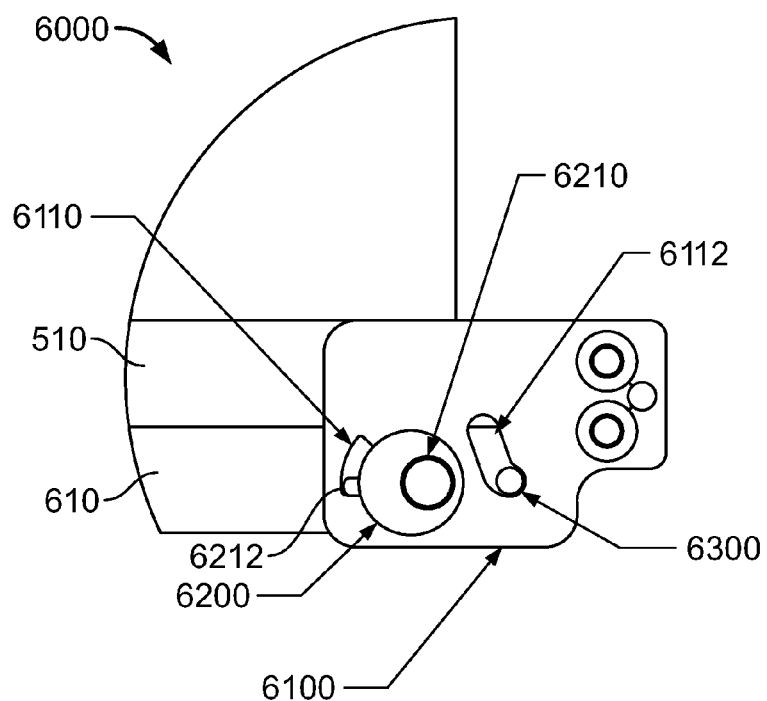
FIGS. 14-15 are side views of a hinge.
Figure 15:
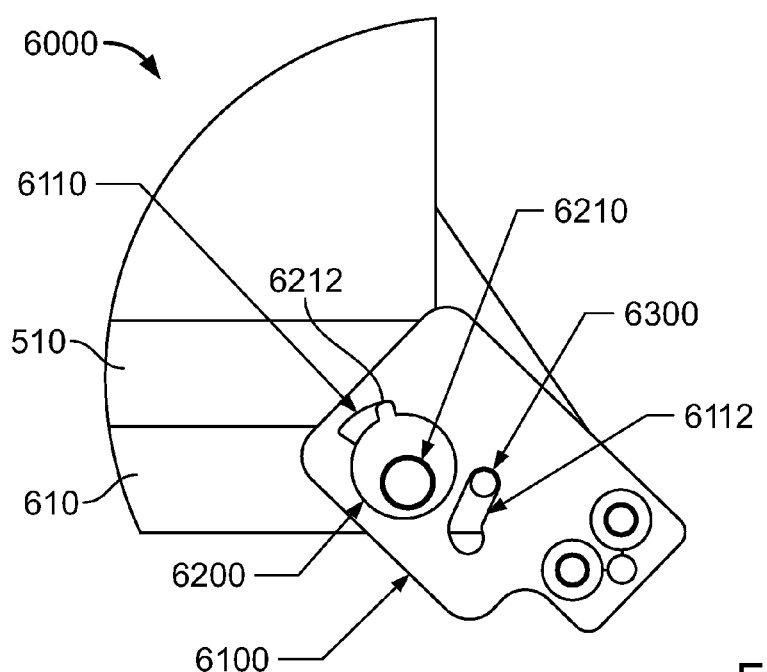

FIG. 14 illustrates the eccentric hinge 6000 in a locked position. FIG. 15 illustrates the eccentric hinge 6000 in an un-locked position. The eccentric hinge 6000 includes a hinge block 6100 secured to the clamp bar 632 and placed over an eccentric cam 6200 secured to a shaft 6210. The hinge block 6100 defines a limitation slot 6110 which receives a cam protrusion 6212. The limitation slot 6110 is positioned to provide an over-center locking action to lock the clamp 630.

In some examples, the hinge block 6100 defines a cam path 6112 which retains a dowel pin 6300 secured to the mount system base 610. The cam path 6112 controls the rotational travel limits of the hinge block 6100. The shaft 6210 is common to both eccentric cams 6200. The shape of the cam path 6112 allows for linear movement of the eccentric cam 6200. Rotation of the eccentric cam 6200 produces the linear force component that clamps the proton applicator 500 in place with accuracy and repeatability. Use of the eccentric cam 6200 provides a strong mechanical force advantage over a conventional non-eccentric clamp. The eccentric hinge 6000 includes an extension spring 6400 to control the timing of engagement of the eccentric cam 6200. The spring force is balanced, such that as the clamp bar 632 is rotating into the lock position the actuation of the linear movement of the eccentric cam 6200 is held back.

Figure 16:
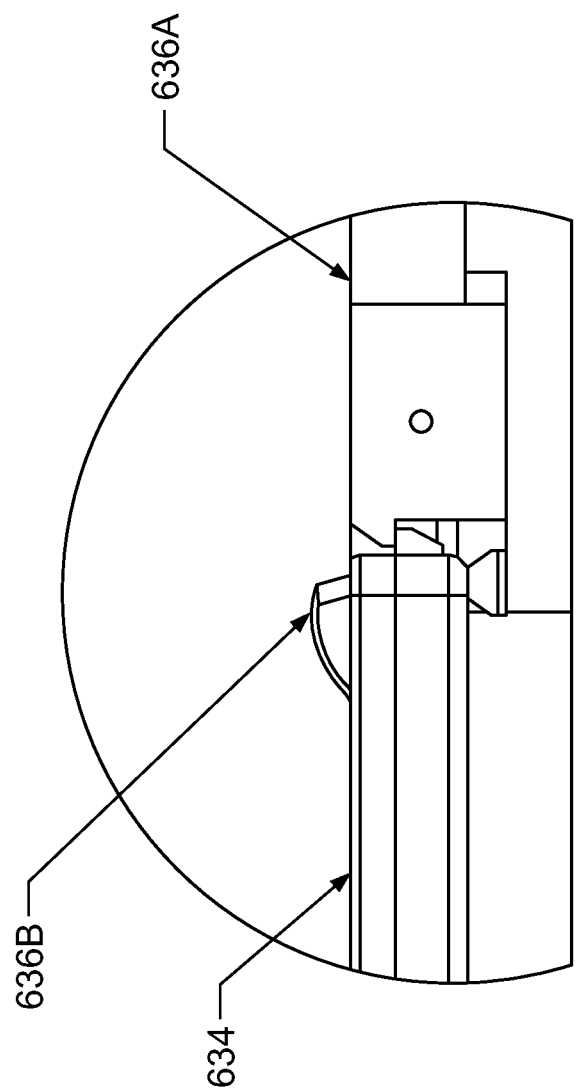
FIG. 16 is a side view of a handle latch.

Referring to FIG. 16, when the hinge block 6100 and clamp bar 632 are at a rotational limit of travel, the linear component of the eccentric cam 6200 engages and locks the proton applicator 500 into position. To disengage the clamp 630, the same actions may be performed in reverse. Both forward and reverse movements may be controlled by the rotation of the lock handle 634. The lock handle 634 is locked into position with the aid of the secondary release latch 636 which is compression spring loaded. Engagement of the secondary release latch 636 into a secondary retaining block 637 latches the lock handle 634.

Figure 17:
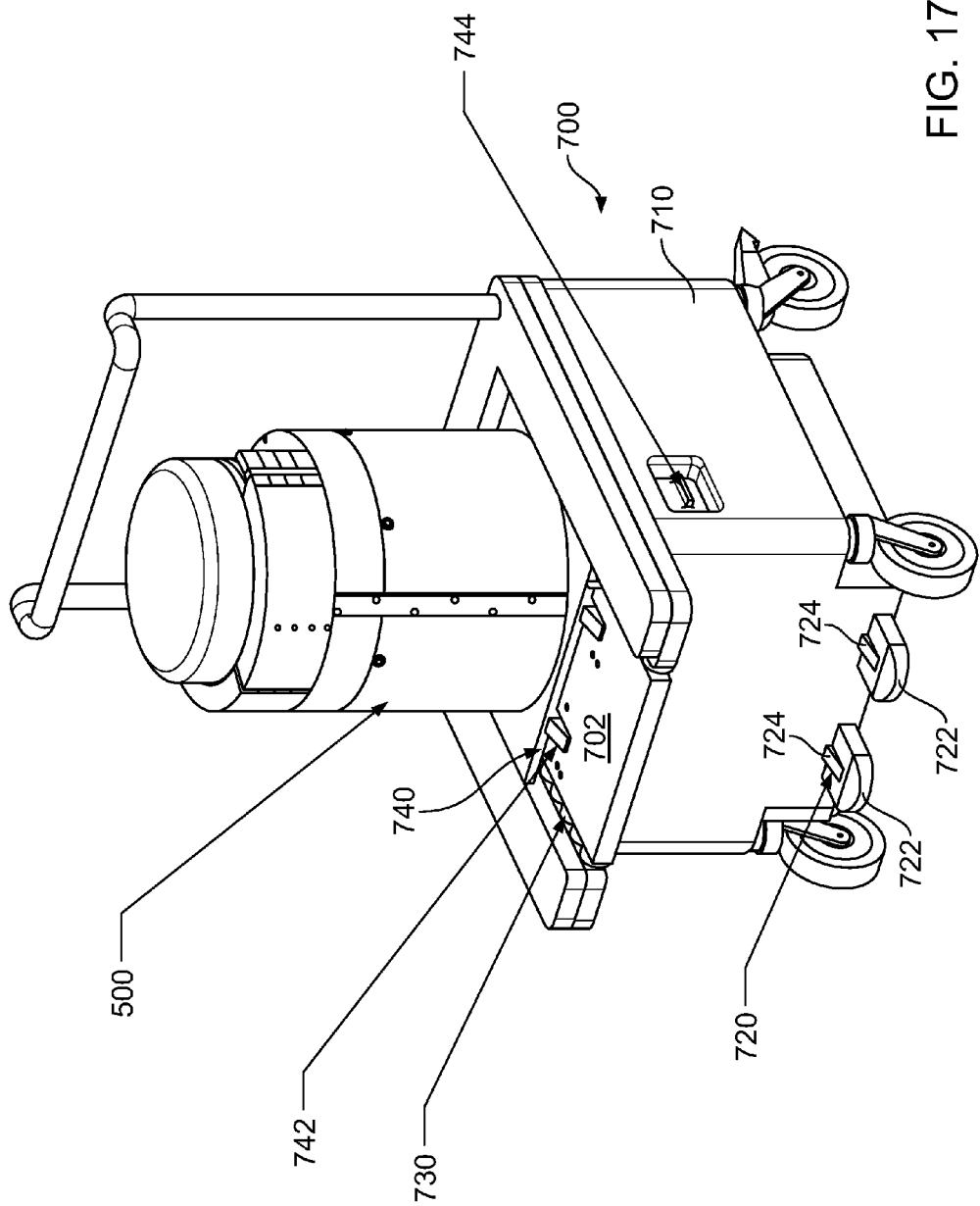
FIGS. 17-19 are perspective views of a transport cart.
Figure 18:
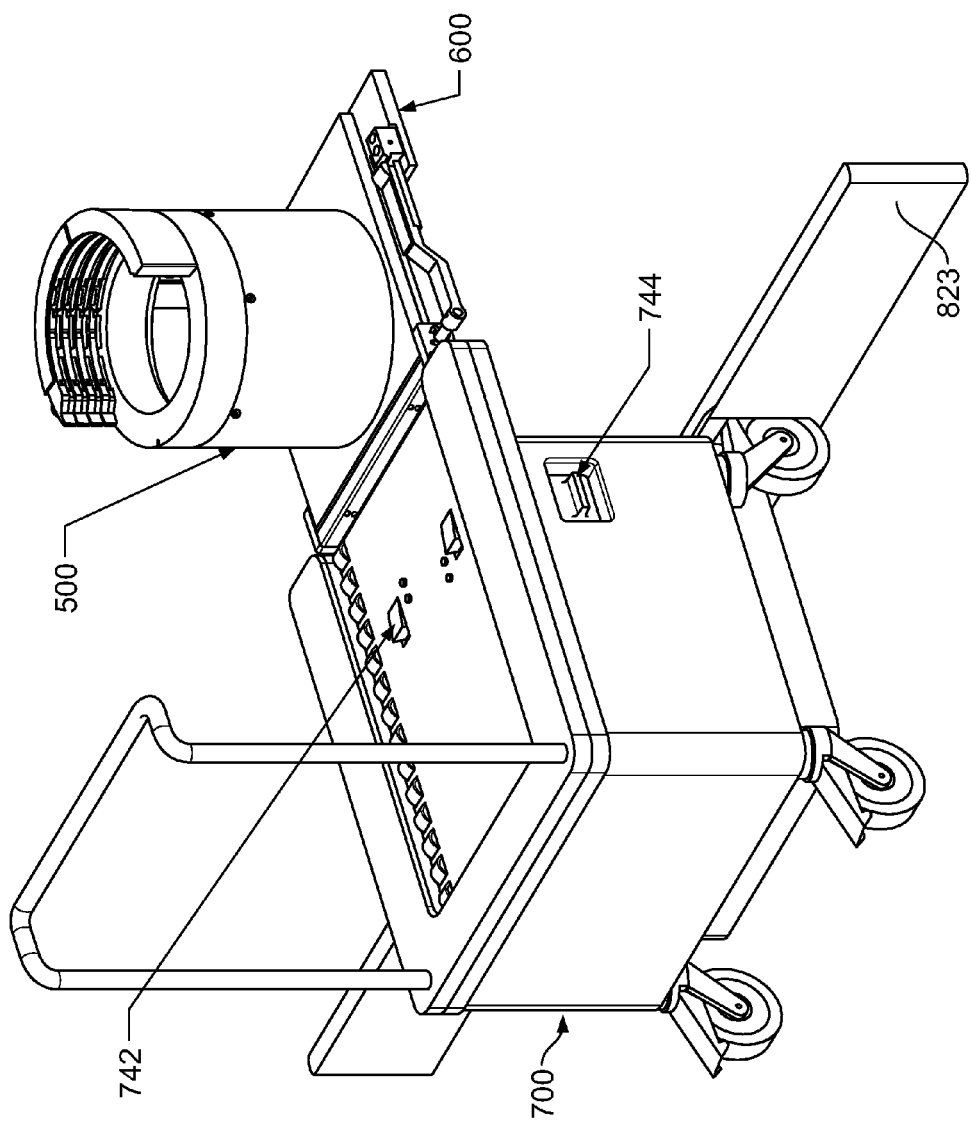
Figure 19:
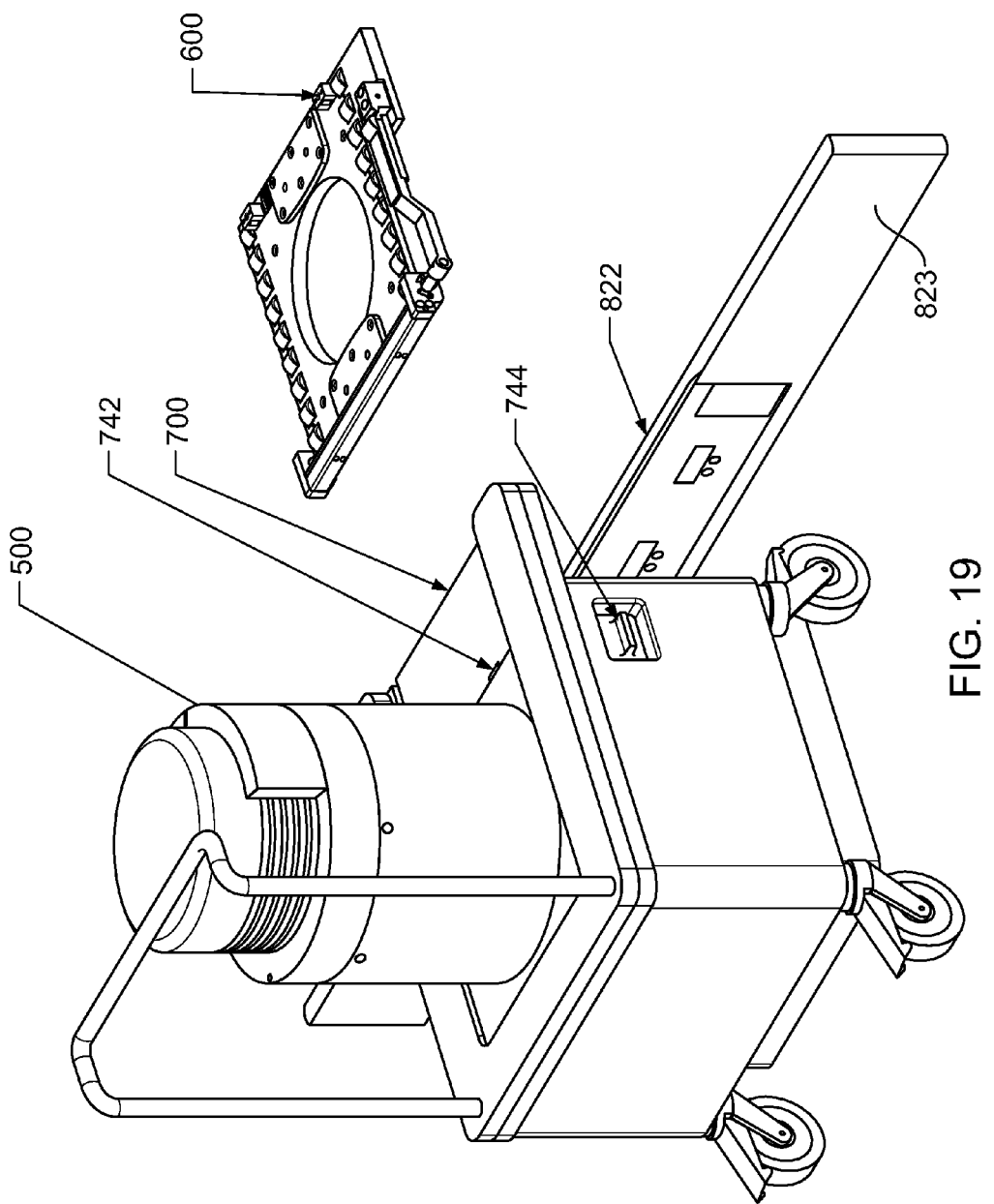

Referring to FIGS. 17-19, the applicator transport cart 700 may be used to transport and change proton applicators 500 onto and off of the C-Inner Gantry (CIG). The applicator transport cart 700 includes a support body 710 having a top portion 702 on which the proton applicator 500 rests. In one example, two different sized proton applicators 500 may be provided with a radiation beam delivery system: a large field proton applicator 500 (25 cm treatment field diameter) and a small field proton applicator 500 (14 cm treatment field diameter). Both proton applicators 500 are of significant weight and size and must be transported and changed safely by a radiation therapist. Changing of the proton applicators 500 should by completed in a timely manner in order to increase the number of patient treatments per day. Each proton applicator 500 may have a transport cart 700 that docks into a side of the CIG.

Figure 20:
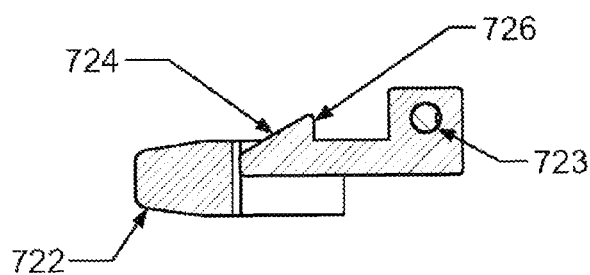
FIGS. 20-21 are side views of a transport cart docking interlock.
Figure 21:
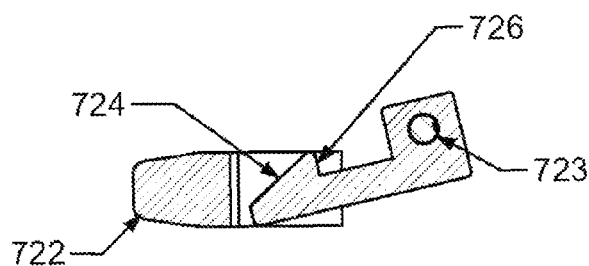

Referring to FIGS. 20-21, a docking interlock 720 prevents the transport cart 700 from backing out of the C-Inner Gantry while docked. The docking interlock 720 aligns the transport cart 700 both laterally and vertically with tapered protruding tongues 722 that dock into an associated slotted docking plate 822. The docking plate 822 resides on the CIG. The docking interlock 720 locks into the CIG with spring loaded ramped cams 724 that catch into the opposite side of the docking plate 822 with a retention surface 726. The transport cart 700 includes a plurality of rollers 730 disposed on the top portion 702 of the transport cart 700. The rollers 730 are positioned to support the proton applicator 500.

Figure 22:
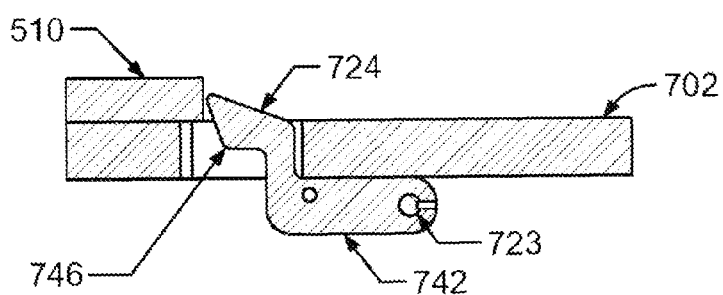
FIGS. 22-23 are side views of a proton applicator interlock.
Figure 23:
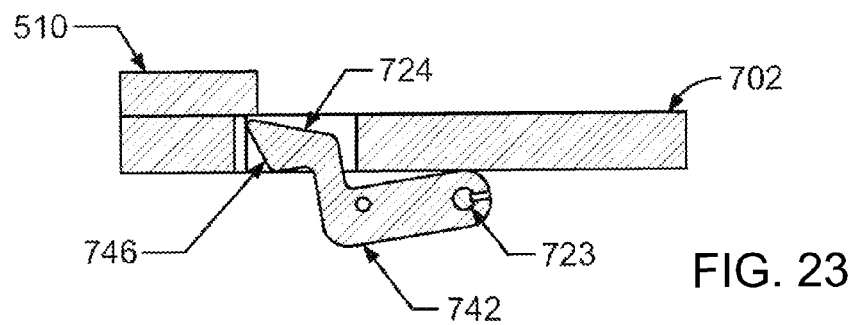

Referring to FIGS. 22-23, the transport cart 700 includes an applicator interlock 740 which retains the proton applicator 500 on the transport cart 700. In some implementations, the applicator interlock 740 includes at least one ramped spring loaded locking cam 742 disposed on the top portion 702 of the transport cart 700. An applicator release handle 744 on the transport cart 700 is configured to engage and disengage the cam(s) 740. As the proton applicator 500 is pushed onto the cart 700, the proton applicator 500 moves over the cam 742, pushing it down into the top portion 702 until the proton applicator 500 reaches an end of travel. At an end of travel, the ramped cam 742 is exposed and free to spring up to a spring biased position, holding the proton applicator 500 in place with a retention surface 746 on the ramped cam 742. The applicator interlock 740 is similar to the docking interlock 720 by utilizing similar types of ramped cam devices to lock a device into position.

To transfer the applicator 500 off the transport cart 700 and onto the applicator mount system 600, the eccentric locking clamp 630 of the applicator mount system 600 is disengaged to the un-locked position. The applicator release handle 744 on the transport cart 700 is disengaged and the therapist pushes the proton applicator 500 off the transport cart 700 and onto the applicator mount system 600. The proton applicator 500 travels on rollers 730 from the transport cart 700 to rollers 620 of the applicator mount system 600. The locking clamp 630 of the applicator mount system 600 is engaged into its locked position. The docking interlock 720 is disengaged (e.g. by an associated handle) and the transport cart 700 is released from the CIG and moved away to a storage area. Removing the proton applicator 500 involves similar steps as described above. However, when the proton applicator 500 is moved from the CIG to the transport cart 700 the user does not need to actuate the applicator release handle 742 on the transport cart 700.

The claims are not limited to the implementations described above. Elements of different implementations may be combined to form other implementations not specifically described herein.

Other implementations are within the scope of the following claims.

The invention claimed is:

1. A system for providing a particle beam to a patient, comprising:
   a first device to limit horizontal application of the particle beam;
   a second device to provide vertical compensation for the first device relative to the patient, the second device comprising a mounting structure, and the first device being substantially aligned to the second device at the mounting structure;
   a stationary yoke comprising a first end and a second end, the stationary yoke attaching to the first device and the second device; and
   a catch arm attached pivotally secured to the first end of the yoke, the catch arm being configured to attach to the first device and the second device, and the catch arm being configured to pivot about the first end of the stationary yoke both towards, and away from, the mounting structure.

2. The system of claim 1, wherein the first device comprises a patient aperture having an area for inhibiting passage of the particle beam; and
   wherein the second device comprises a range compensator that affects a distance between the patient and the first device.

3. The system of claim 1, wherein the first device comprises first notch features and the mounting structure comprises second notch features, the first notch features aligning to the second notch features; and
   wherein the stationary yoke comprises a first structure configured to mate to the first notch features that are aligned and the catch arm comprises a second structure configured to mate to the second notch features that are aligned.

4. The system of claim 1, wherein the first device, the second device, the stationary yoke, and the catch arm form an integrated structure; and
   wherein the system further comprises a C-shaped inner gantry on which the integrated structure is mounted.

5. The system of claim 1, wherein the stationary yoke comprises an indicator switch to detect locked and unlocked positions of the catch arm.

6. The system of claim 1, wherein the mounting structure comprises a rim and wherein the stationary yoke and the catch arm each comprise a groove to which the rim interfaces.

7. The system of claim 1, further comprising a catch arm locking feature defined by the yoke to inhibit rotation of the catch arm, the catch arm locking feature for engaging a catch arm lock, the catch arm lock comprising a latch plate that is positionable to engage the catch arm locking feature.

8. The system of claim 7, wherein the catch arm locking feature is configured to spring bias the latch plate.

9. The system of claim 7, further comprising at least one spring biased plunger on the stationary yoke and configured to urge the first device against the locking feature.

10. A system for providing a particle beam to a patient, comprising:
    a structure to limit a delivery area of the particle beam to the patient, the structure comprising a rim and notches around the rim; and
    an arm having a shape that corresponds to a shape of at least part of a perimeter of the structure, the arm having a groove that mates to the rim and protrusions that mate to the notches, the arm comprising a first part and a second part, the first part being configured to pivot relative to the second part.

11. The system of claim 10, wherein the structure comprises a patient aperture having an area for inhibiting passage of the particle beam; and
    wherein the structure comprises a range compensator that affects a distance between the patient and the first device.

12. The system of claim 11, wherein the notches comprise first notches on the patient aperture and second notches on the range compensator, the first notches aligning to the second notches; and
    wherein the protrusions comprise a first protrusion configured to mate to the first notches that are aligned and a second protrusion configured to mate to the second notches that are aligned.

13. The system of claim 10, wherein the structure and the arm form an integrated structure; and
    wherein the system further comprises a C-shaped inner gantry on which the integrated structure is mounted.

14. The system of claim 10, wherein the arm comprises an indicator switch to detect locked and unlocked positions of the first part of the arm.

15. The system of claim 10, further comprising at least one spring biased plunger on the second part of the arm.

16. The system of claim 10, further comprising a catch arm locking feature defined by the arm to inhibit rotation of the first part, the catch arm locking feature for engaging a catch arm lock, the catch arm lock comprising a latch plate that is positionable to engage the catch arm locking feature.

17. The system of claim 16, wherein the catch arm locking feature is configured to spring bias the latch plate.

\* \* \* \* \*